United States Patent
Segale et al.

(10) Patent No.: US 10,227,636 B2
(45) Date of Patent: *Mar. 12, 2019

(54) DYNAMIC AUTOFOCUS METHOD AND SYSTEM FOR ASSAY IMAGER

(71) Applicant: Illumina, Inc., San Diego, CA (US)

(72) Inventors: Darren Robert Segale, San Diego, CA (US); John A. Moon, San Diego, CA (US); Hongji Ren, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 358 days.

This patent is subject to a terminal disclaimer.

(21) Appl. No.: 15/009,272

(22) Filed: Jan. 28, 2016

(65) Prior Publication Data

US 2016/0304940 A1    Oct. 20, 2016

Related U.S. Application Data

(63) Continuation of application No. 13/853,492, filed on Mar. 29, 2013, now Pat. No. 9,404,737, which is a
(Continued)

(51) Int. Cl.
*G01B 11/24*     (2006.01)
*C12Q 1/6818*    (2018.01)
(Continued)

(52) U.S. Cl.
CPC ......... *C12Q 1/6818* (2013.01); *C12Q 1/6874* (2013.01); *G01B 11/24* (2013.01);
(Continued)

(58) Field of Classification Search
CPC ....... G01N 2015/1452; G01N 15/1463; G01N 21/6458; G06K 9/00127; H04N 5/23212; G01B 9/02063
(Continued)

(56) References Cited

U.S. PATENT DOCUMENTS 5,570,691 A    11/1996    Wright et al.
5,647,025 A    7/1997     Frost et al.
(Continued)

*Primary Examiner* — Tri T Ton
*Assistant Examiner* — Rebecca C Bryant
(74) *Attorney, Agent, or Firm* — Illumina, Inc.

(57) ABSTRACT

A method for scanning a microarray, including (a) providing a microarray to an optical scanner, wherein the microarray includes a surface having features having different target molecules; (b) scanning the surface in the x or y direction to acquire optical signals from the features at sequential regions of the surface, wherein the focus setting between the optical scanner and the surface is dynamically controlled in real time by repeatedly (i) adding a predetermined focal offset, thereby introducing an error in the focus setting, and (ii) adjusting the focus setting to reduce the error in the focus setting, thereby acquiring the optical signals from different regions at different degrees of focus such that a subset of the regions that are scanned have an introduced focus error; and (c) analyzing the optical signals that are obtained at the different degrees of focus to identify the different target molecules.

14 Claims, 12 Drawing Sheets

Related U.S. Application Data continuation of application No. 12/638,770, filed on Dec. 15, 2009.

(60) Provisional application No. 61/122,550, filed on Dec. 15, 2008.

(51) Int. Cl.
  *G01N 21/64* (2006.01)
  *G02B 21/24* (2006.01)
  *H04N 5/232* (2006.01)
  *C12Q 1/6874* (2018.01)
  *G01B 9/02* (2006.01)

(52) U.S. Cl.
  CPC ..... *G01N 21/6428* (2013.01); *G01N 21/6458* (2013.01); *G02B 21/244* (2013.01); *H04N 5/23212* (2013.01); *G01B 9/02063* (2013.01)

(58) Field of Classification Search
  USPC .......................................................... 356/624
  See application file for complete search history.

(56) References Cited

U.S. PATENT DOCUMENTS

| | | |
|---|---|---|
| 5,834,758 A | 11/1998 | Trulson et al. |
| 5,981,956 A | 11/1999 | Stern |
| 6,025,601 A | 2/2000 | Trulson et al. |
| 6,597,000 B2 | 7/2003 | Stern |
| 6,741,344 B1 | 5/2004 | Stern et al. |
| 7,329,860 B2 | 2/2008 | Feng et al. |
| 7,397,510 B2 | 7/2008 | Yasuda |
| 7,706,632 B2 * | 4/2010 | Gouch .................. G06K 9/209 345/629 |
| 7,900,836 B2 | 3/2011 | Moon et al. |
| 8,310,531 B2 | 11/2012 | Nandy |
| 2002/0051992 A1 | 5/2002 | Bridgham et al. |
| 2002/0131032 A1 | 9/2002 | Tsuji et al. |
| 2004/0031779 A1 | 2/2004 | Cahill et al. |
| 2004/0085443 A1 | 5/2004 | Kallioniemi et al. |
| 2006/0209309 A1 | 9/2006 | Feng |
| 2008/0266440 A1 | 10/2008 | Yazdanfar et al. |
| 2011/0115897 A1 | 5/2011 | Najmabadi et al. |

* cited by examiner

DYNAMIC AUTOFOCUS METHOD AND SYSTEM FOR ASSAY IMAGER

CROSS REFERENCE TO RELATED APPLICATIONS

This application is a continuation of U.S. application Ser. No. 13/853,492, filed Mar. 29, 2013, which is a continuation of U.S. application Ser. No. 12/638,770, filed Dec. 15, 2009, which claims the benefit of U.S. Provisional Application No. 61/122,550, filed Dec. 15, 2008 each of which is incorporated herein by reference in its entirety.

BACKGROUND OF THE INVENTION

Embodiments of the present invention relate generally to sample imaging, and more specifically to dynamic autofocus methods and systems for assay imaging.

A wide variety of optical systems exist that capture images of an area of interest on assays for subsequent analysis. Each image may be obtained by detecting light produced across an entire area of interest on an assay substrate at one point in time. Alternatively, each image may be obtained by scanning an illumination source across the area of interest while detecting light produced at the current illuminated spot. For example, a series of successive line scans of a tightly focused illumination beam may be directed across the area of interest, such as in a raster manner, to build up a two-dimensional detected image.

Optical systems exist that image microarrays of silica beads that self assemble in microwells on substrates (e.g., fiber optic bundles or planar silica slides). When randomly assembled on the substrate, the beads have a uniform spacing of ~5.7 microns. Each bead is covered with hundreds of thousands of copies of a specific oligonucleotide that act as the capture sequences in assays. Imaging of microparticles provides a robust detection method to multiplex assays requiring high precision, accuracy, and speed. Microbeads are useful for numerous bioassays including genotyping, gene expression, and protein-based assays.

Imaging systems exist that are used in DNA sequencing that uses parallel analysis of unamplified, or amplified single molecules, either in the form of planar arrays or on beads. The methodology used to analyze the sequence of the nucleic acids in such sequencing techniques is often based on the detection of fluorescent nucleotides or oligonucleotides. The detection instrumentation used to read the fluorescence signals on such arrays may be based on either epifluorescence or total internal reflection microscopy. One detection instrument has been proposed that use an optical sequencing-by-synthesis (SBS) reader. The SBS reader includes a laser that induces fluorescence from a sample within water channels of a flowcell. The fluorescence is emitted and collected by imaging optics which comprises one or more objective lens and tube lens. As the fluorescence travels along an optics path within the imaging optics, but prior to reaching a detection camera, the fluorescence propagates through an interference emission filter.

Optical imagers include, among other things, a light source to illuminate a sample in the region of interest, one or more detectors, and optical components to direct light from the region of interest to the detector(s). The optical imagers also include a focus mechanism that maintains focus of the optical components on the region of interest in order that light received at the detectors is received in focus.

However, conventional optical imagers have experienced certain limitations. Conventional focus mechanisms are often implemented as a separate subsystem including a separate focus light source and focus detector. The focus light is directed onto the sample and reflected to the focus detector. The light received at the focus detector is analyzed and used to adjust the optical components to maintain focus. However, conventional focus mechanisms utilize components separate and part from the optical components that are used to capture images of the region of interest, thereby increasing the cost, complexity, and number of parts that may potentially fail.

Further, in certain optical systems, the image cannot be captured until after the focus mechanism first performs focus measurements and adjusts the optical components relative to the area of interest. Optical systems that first measure and adjust the focus, before capturing images exhibit increased time between capture of images. Cycle time represents the rate at which images may be acquired (either through line scan or through snap-shot type detection). The image acquisition rate is slower for systems that must first ascertain the focal position prior to image acquisition.

Moreover, conventional optical systems that use separate focus mechanisms adjust focus based on reflectance measurements by the focus mechanism. The reflectance measurement is derived from a focus light beam and focus detector that are separate and distinct from the actual data image captures for the area of interest. Therefore, the reflectance measurement represents an indirect estimate of the correct focal position for the actual data image. When the focus mechanism loses calibration with the optical components, the focal plane of the focus mechanism may become misaligned with, or slightly differ from, the actual or true focal plane associated with the actual image. Thus, the focus mechanism may adjust the focal plane in a manner that is incomplete or inaccurate.

It is desirable to provide improved methods and systems to focus dynamically sample imaging systems.

BRIEF DESCRIPTION OF THE INVENTION

In accordance with one embodiment, a method is provided for controlling focus dynamically of a sample imager. The method includes scanning a sample with an optical assembly by apportioning the sample into a plurality of regions defined by a scan pattern. The optical assembly has a focal setting with respect to the sample. The method also includes shifting the focal setting of the optical assembly during scanning of the sample whereby the images have an associated degree of focus corresponding to the focal setting of the optical assembly. The method further includes analyzing the images to obtain at least two focus scores. The focus scores represent a degree to which the optical assembly was in focus when detecting the images. The method also includes adjusting the focus setting based on a function of the at least two focus scores.

In another embodiment, an optical imaging system is provided. The imaging system includes a sample holder to receive a sample and an optical assembly to scan the sample. The optical assembly apportions the sample into regions defined by a scan pattern. The optical assembly has a focal setting with respect to the sample. The imaging system also includes a focus control module to introduce a shift by a predetermined extent into the focal setting of the optical assembly. The imaging system also includes a detector to detect images representative of at least two regions from the sample. The images each have an associated degree of focus corresponding to the focal setting of the optical assembly. The imaging system also includes an image analysis module to analyze the images to obtain at least two focus scores. Each of the focus scores represents a degree to which the optical assembly was in focus when detecting the image. The image analysis module may also determine a desired focal setting based on a function of the at least two focus scores. The focus control module adjusts the focus setting based on the desired focal setting.

In a further embodiment, a method is provided for controlling focus dynamically of a sample imager. The method includes detecting a first region of a sample with an optical assembly thereby obtaining a first image. The optical assembly has a first focal setting with respect to the sample. The method also includes analyzing a first image to obtain a first focus score. The first focus score represents a degree to which the optical assembly was in focus when detecting the first image. The method further includes shifting the focal setting of the optical assembly by a predetermined extent to a second focal setting and detecting a second region of the sample with the optical assembly at the second focal setting thereby obtaining a second image. The method also includes analyzing the second image to obtain a second focus score. The second focus score represents a degree to which the optical assembly was in focus when detecting the second image. Furthermore, the method includes determining a desired focal setting for the optical assembly based on a function of at least the first focus score and the second focus score.

In a further embodiment, a method for controlling focus dynamically of a sample imager is provided. The method includes detecting a plurality of images of a sample. The plurality of images include information relating to detected light signals from the sample. The plurality of images include first and second images. The method also includes analyzing the first and second images to obtain respective focus scores. The focus scores represent a degree to which the optical assembly was in focus when detecting the first and second images. The focus scores of the first and second images are different. The method also includes comparing the focus scores of the first and second images and relatively shifting the sample with respect to the optical assembly based upon said comparison of the focus scores.

Optionally, the first image may correspond to light signals within a first spectral band that are emitted from a first label in the sample and the second image may correspond to light signals within a second spectral band that are emitted from a second label in the sample. Furthermore, the optical assembly may have different optimal focal planes for the first and second labels.

Also optionally, the first and second images may be of adjacent scan regions of the sample. The focal setting of the optical assembly may be shifted a predetermined extent before obtaining the second image.

In yet another embodiment, a method for controlling focus dynamically of a sample imager is provided. The method includes obtaining first and second images of a scan region of a sample. The sample is positioned relative to an optical assembly. The first and second images include information relating to detected light signals from first and second labels in the sample, respectively. The method also includes analyzing the first and second images to obtain first and second focus scores. The focus scores represent a degree to which the optical assembly was in focus when detecting the first and second images. The method further includes comparing the first and second focus scores and relatively shifting the sample with respect to the optical assembly based upon said comparison of the first and second focus scores. The sample has a modified position relative to the optical assembly.

DETAILED DESCRIPTION OF THE INVENTION

Figure 1:
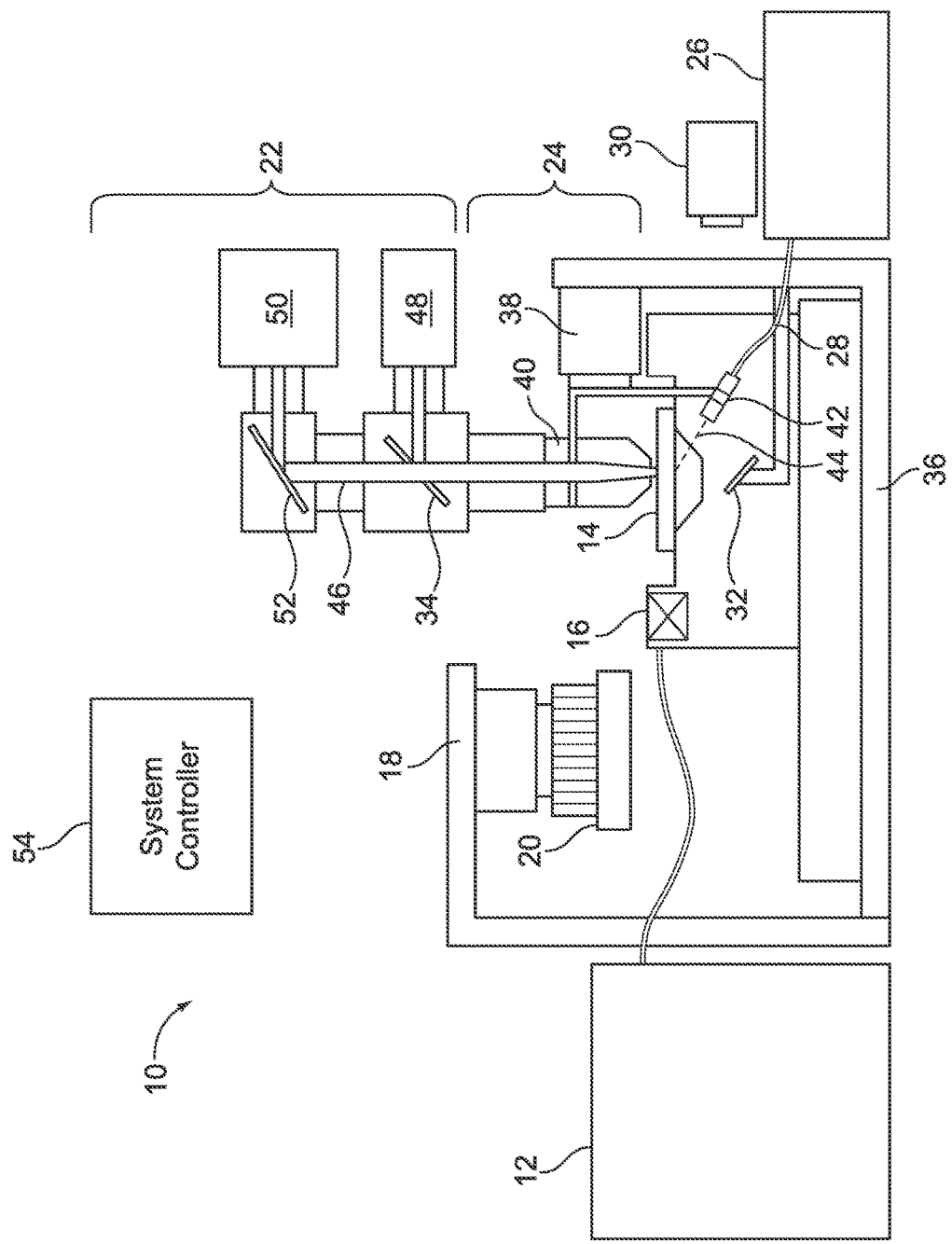
FIG. 1 shows an exemplary optical imaging system formed in accordance with an embodiment.

FIG. 1 illustrates an optical imaging system 10 that is formed in accordance with an embodiment. By way of example, the imaging system 10 may be constructed to include various components and assemblies as described in PCT application PCT/US07/07991, titled "System and Devices for Sequence by Synthesis Analysis", filed Mar. 30, 2007 and/or to include various components and assemblies as described in PCT application PCT/US2008/077850, titled "Fluorescence Excitation and Detection System and Method", filed Sep. 26, 2008, for both of which the complete subject matter are incorporated herein by reference in their entirety. In particular embodiments, the imaging system 10 can include various components and assemblies as described in U.S. Pat. No. 7,329,860, of which the complete subject matter is incorporated herein by reference in its entirety.

As can be seen in FIG. 1, a fluid delivery module 12 directs the flow of reagents (e.g., fluorescent nucleotides, buffers, enzymes, cleavage reagents, etc.) to (and through) flowcell 14 and waste valve 16. The flow cell 14 may represent a substrate having one or more samples provided on or in the substrate. In particular embodiments, the flowcell 14 comprises clusters of nucleic acid sequences (e.g., of about 200-1000 bases in length) to be sequenced which are optionally attached to the substrate of the flowcell 14, as well as optionally to other components. The flowcell 14 may also comprise an array of beads, where each bead optionally contains multiple copies of a single sequence.

The imaging system 10 also comprises temperature station actuator 18 and heater/cooler 20, which can optionally regulate the temperature of conditions of the fluids within the flowcell 14. The flowcell 14 is monitored, and sequencing is tracked, by detection assembly 22 which can interact with focusing assembly 24. Excitation assembly 26 (e.g., one or more excitation lasers within an assembly) acts to illuminate fluorescent sequencing reactions within the flowcell 14 via laser illumination through fiber optic 28 (which can optionally comprise one or more re-imaging lenses, a fiber optic mounting, etc.). Low watt lamp 30 (optional), mirror 32, and reverse dichroic beam splitter 34 are also presented in the embodiment shown. Additionally, mounting stage 36, allows for proper alignment and movement of the flowcell 14, temperature station actuator 18, detection assembly 22, etc. in relation to the various components of the system. Focus (z-axis) component 38 can also aid in manipulation and positioning of various components such as lens 40 and source emitter 42. The emitter 42 scans one or more samples provided in the flow cell 14 based on a scan pattern. The focus component 38 causes the emitter 42 to move an excitation laser 44 in a raster scan pattern. The detection assembly 22 apportions the sample into regions. The regions can be in the form of blocks or any other shape appropriate to the imaging optics in use. The sample produces at least one of an emission pattern and a transmission pattern that is conveyed along detection path 46 to the detection assembly 22.

The detection assembly 22 includes a label detector 48, a code detector 50, a dichroic beam splitter 34, and mirror 52. A system controller 54 controls overall operation of the imaging system 10. Such components are optionally organized upon a framework and/or enclosed within a housing structure. It will be appreciated that the illustrations herein are of exemplary embodiments and are not necessarily to be taken as limiting. Thus, for example, different embodiments can comprise different placement of components relative to one another (e.g., embodiment A comprises a heater/cooler as in FIG. 1, while embodiment B comprises a heater/cooler component beneath the flowcell, etc.).

Optionally, the imaging system 10 may be utilized for detection of samples on microarrays. A microarray is a population of different probe molecules that is attached to one or more substrates such that the different probe molecules can be differentiated from each other according to relative location. An array can include different probe molecules, or populations of the probe molecules, that are each located at a different addressable location on a substrate. Alternatively, a microarray can include separate substrates, such as beads, each bearing a different probe molecule, or population of the probe molecules, that can be identified according to the locations of the substrates on a surface to which the substrates are attached or according to the locations of the substrates in a liquid. Exemplary arrays in which separate substrates are located on a surface include, without limitation, a Sentrix® Array or Sentrix® BeadChip Array available from Illumina®, Inc. (San Diego, Calif.) or others including beads in wells such as those described in U.S. Pat. Nos. 6,266,459, 6,355,431, 6,770,441, and 6,859,570; and PCT Publication No WO 00/63437, each of which is hereby incorporated by reference. Other arrays having particles on a surface include those set forth in US 2005/0227252; WO 05/033681, and WO 04/024328, each of which is hereby incorporated by reference.

Further examples of commercially available microarrays that can be used include, for example, an Affymetrix® GeneChip® microarray or other microarray synthesized in accordance with techniques sometimes referred to as VLSIPS™ (Very Large Scale Immobilized Polymer Synthesis) technologies as described, for example, in U.S. Pat. Nos. 5,324,633; 5,744,305; 5,451,683; 5,482,867; 5,491,074; 5,624,711; 5,795,716; 5,831,070; 5,856,101; 5,858.659; 5,874,219; 5,968,740; 5,974,164; 5,981,185; 5,981,956; 6,025,601; 6,033,860; 6,090,555; 6,136,269; 6,022,963, 6,083,697; 6,291,183; 6,309,831; 6,416,949; 6,428,752 and 6,482,591, each of which is hereby incorporated by reference. A spotted microarray can also be used in a method according to an embodiment of the invention. An exemplary spotted microarray is a CodeLink™ Array available from Amersham Biosciences. Another microarray that is useful is one that is manufactured using inkjet printing methods such as SurePrint™ Technology available from Agilent Technologies.

The systems and methods set forth herein can be used to detect the presence of a particular target molecule in a sample contacted with the microarray. This can be determined, for example, based on binding of a labeled target analyte to a particular probe of the microarray or due to a target-dependent modification of a particular probe to incorporate, remove, or alter a label at the probe location. Any one of several assays can be used to identify or characterize targets using a microarray as described, for example, in U.S. Patent Application Publication Nos. 2003/0108867, 2003/0108900; 2003/0170684; 200310207295; or 2005/0181394, each of which is hereby incorporated by reference.

Exemplary labels that can be detected in accordance with embodiments of the invention, for example, when present on a microarray include, but are not limited to, a chromophore; luminophore; fluorophore; optically encoded nanoparticles; particles encoded with a diffraction-grating; electrochemiluminescent label such as Ru(bpy)$_3^{2+}$; or moiety that can be detected based on an optical characteristic. Fluorophores that are useful in the invention include, for example, fluorescent lanthanide complexes, including those of Europium and Terbium, fluorescein, rhodamine, tetramethylrhodamine, eosin, erythrosin, coumarin, methyl-coumarins, pyrene, Malacite green, Cy3, Cy5, stilbene, Lucifer Yellow, Cascade Blue™, Texas Red, alexa dyes, phycoerythin, bodipy, and others known in the art such as those described in Haugland, *Molecular Probes Handbook*, (Eugene, Oreg.) 6th Edition; The Synthegen catalog (Houston, Tex.), Lakowicz, *Principles of Fluorescence Spectroscopy,* 2nd Ed., Plenum Press New York (1999), or WO 98/59066, each of which is hereby incorporated by reference.

Any of a variety of microarrays known in the art, including, for example, those set forth previously herein, can used in embodiments of the invention. A typical microarray contains sites, sometimes referred to as features, each having a population of probes. The population of probes at each site is typically homogenous having a single species of probe, but in some embodiments the populations can each be heterogeneous. Sites or features of an array are typically discrete, being separated with spaces between each other. The size of the probe sites and/or spacing between the sites can vary such that arrays can be high density, medium density or lower density. High density arrays are characterized as having sites separated by less than about 15 μm. Medium density arrays have sites separated by about 15 to 30 μm, while low density arrays have sites separated by greater than 30 μm. An array useful in the invention can have sites that are separated by less than 100 μm, 50 μm, 10 μm, 5 μm, 1 μm, or 0.5 μm. An apparatus or method of an embodiment of the invention can be used to image an array at a resolution sufficient to distinguish sites at the above densities or density ranges.

Optionally, the imaging system 10 may be utilized for sequencing-by-synthesis (SBS). In SBS, a plurality of fluorescently labeled modified nucleotides are used to sequence dense clusters of amplified DNA (possibly millions of clusters) present on the surface of a substrate (e.g., a flowcell). The flowcells 14 may contain nucleic acid samples for sequencing where the flowcells 14 are placed within the appropriate flowcell holders. The samples for sequencing can take the form of single nucleic acid molecules, amplified populations of a nucleic acid molecule template in the form of clusters, or beads comprising one or more molecules of nucleic acid. The nucleic acids are prepared such that they comprise an oligonucleotide primer adjacent to an unknown target sequence. To initiate the first SBS sequencing cycle, one or more differently labeled nucleotides, and DNA polymerase, etc., are flowed into/through the flowcell by the fluid flow subsystem (various embodiments of which are described herein) Either a single nucleotide can be added at a time, or the nucleotides used in the sequencing procedure can be specially designed to possess a reversible termination property, thus allowing each cycle of the sequencing reaction to occur simultaneously in the presence of labeled nucleotides (e.g. A, C, T, G). Where the four nucleotides are mixed together, the polymerase is able to select the correct base to incorporate and each sequence is extended by a single base. One or more lasers may excite the nucleic acids and induce fluorescence. The fluorescence emitted from the nucleic acids is determined by the fluorophores of the incorporated base, and different fluorophores may emit different wavelengths of emission light. Exemplary sequencing methods are described, for example, in Bentley et al., Nature 456:53-59 (2008), which is incorporated herein by reference.

Although embodiments of the invention have been exemplified above with regard to detection of samples on a microarray or flowcell, it will be understood that other samples having features or sites at the above densities can be imaged at the resolutions set forth above. Other exemplary samples include, but are not limited to, biological specimens such as cells or tissues, electronic chips such as those used in computer processors, or the like. Examples of some of the applications of the invention include microscopy, satellite scanners, high-resolution reprographics, fluorescent image acquisition, analyzing and sequencing of nucleic acids, DNA sequencing, sequencing-by-synthesis, imaging of microarrays, imaging of holographically coded microparticles and the like.

The heating/cooling components 20 of the imaging system 10 regulate the reaction conditions within the flowcell channels and reagent storage areas/containers (and optionally the camera, optics, and/or other components), while the fluid flow components allow the substrate surface to be exposed to suitable reagents for incorporation (e.g., the appropriate fluorescently labeled nucleotides to be incorporated) while unincorporated reagents are rinsed away. During laser excitation by the excitation assembly 26, the image/location of emitted fluorescence from the nucleic acids on the substrate is captured by the detection assembly 22, thereby, recording the identity, in the computer component, of the first base for each single molecule, cluster, or bead.

Figure 2:
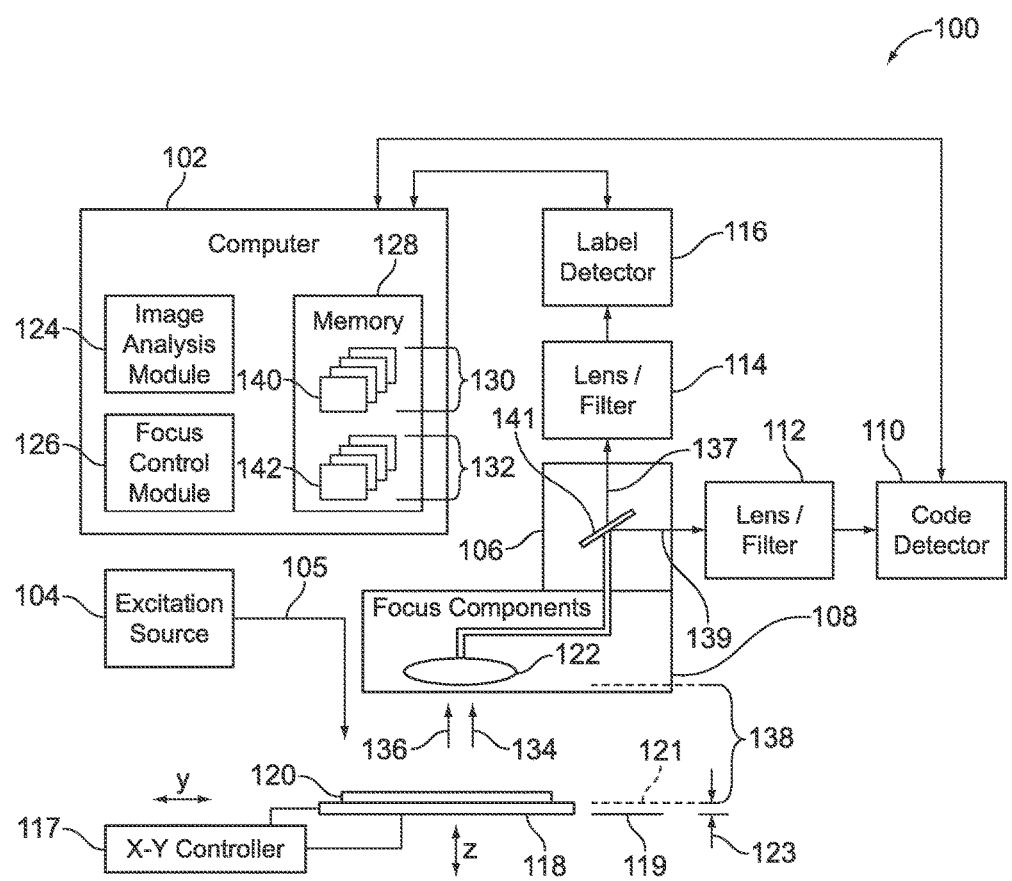
FIG. 2 illustrates a block diagram of an imaging subsystem formed in accordance with an embodiment.
Figure 6:
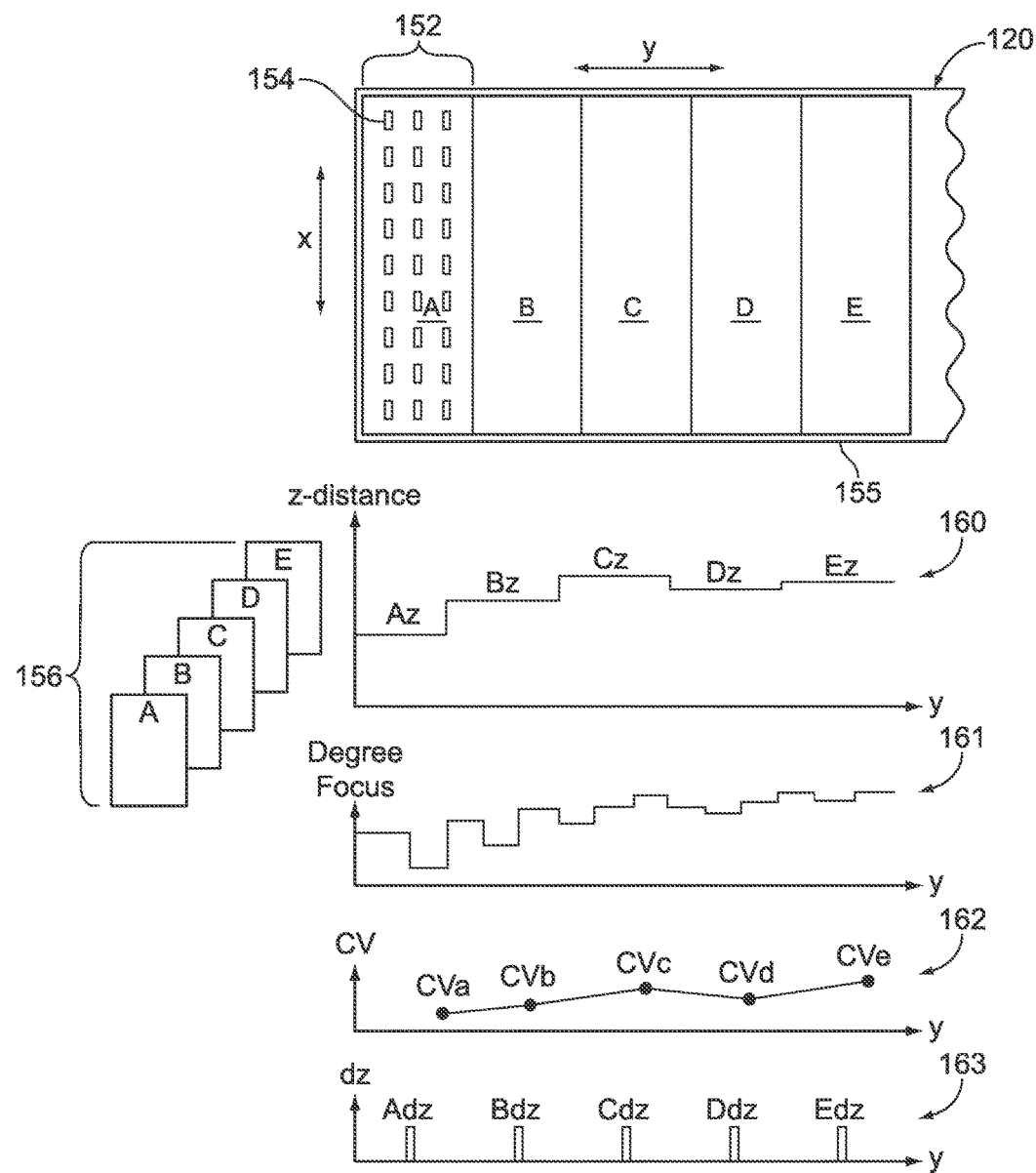
FIG. 6 illustrates a graphical representation of a dynamic focus control operation that may be carried out by the method of FIG. 4 or 5.

FIG. 2 illustrates a more detailed block diagram of an imaging subsystem 100 that may be utilized in the imaging system 10 of FIG. 1. The imaging subsystem 100 includes a computer 102 that receives information and data from, and controls operation of, the other components of the subsystem 100. The imaging subsystem 100 includes one or more excitation source 104, an optical assembly 106, combinations of lenses and filters 114, 112, a code (and/or transmission light) detector 110 and a label detector 116. The imaging subsystem 100 includes a sample holder 118 that is configured to receive a sample 120. For example, the sample 120 may represent micro-particles flowing within a flow cell (e.g. flow cell 14 in FIG. 1) and the holder 118 may represent a flowcell holder. The optical assembly 106 is controlled by the computer 102 to scan the sample 120. During the scanning operation, the optics assembly 106 apportions the sample 120 into regions, for which separate images are detected based on a scan pattern. An x-y controller 117 is mechanically and electrically coupled to the holder 118. The x-y controller 117 moves the holder 118 in the y direction as denoted by arrow y in FIG. 2 during a scanning operation. The x-y controller 117 also moves the holder 118 in the x direction which is orthogonal to the y and z directions. The x direction is shown in FIG. 6.

Settings of at least a portion of the components within the optical assembly 106 may affect a degree to which images are in focus when detected. The position and settings of the optical assembly 106 relative to the sample 120 affect a degree to which images are detected in focus. For example, the optical assembly 106 includes focus components 108 that are focused on an actual focal plane 119. The sample 120 has a preferred focal plane 121, for example, at or below the surface of the sample 120. The focus components 108 are adjusted intermittently or continuously in a control feedback loop in an effort to align and overlay the actual and preferred focal planes 119 and 121. When not aligned, a defocus spread 123 is introduced between the actual and preferred focal planes. As the defocus spread 123 increases, the degree of focus of the image decreases. The focus control module 126 seeks to remove or minimize the defocus spread 123.

Focus related parameters of the focus components 108 in the optical assembly 106 are adjusted (e.g., in position, in orientation) based on focal settings of the optical assembly 106. By way of example, a focal setting may adjust the position of the optical assembly 106 in a z-direction (denoted by arrow z) with respect to the holder 118 and sample 120. As another example, the focus components 108 may include a focus lens 122 that is moved in the z-direction (along the axis denoted by arrow z) toward or away from the sample 120. By moving the lens 122 in the z-direction, the imaging subsystem 100 adjusts a degree of focus of the optical assembly 106 with respect to the sample 120.

Alternatively, the focus setting may adjust the interrelation between components within the focus components 108, such as by moving one or more lens toward or away from one another. The focus components may include a z-motor that is controlled to modulate focus. The motor may be positioned to pivot the lens 122 in an oscillating manner. Optionally, optical path modulation may be achieved with a piezo on a mirror, LCD or electro optics and the like. Any of a variety of methods for adjusting the z position in an optical system can be controlled in accordance with the methods and apparatus set forth herein.

The excitation source 104 generates an excitation light 105 that is directed onto the sample 120. The excitation source 104 may generate one or more laser beams at one or more predetermined excitation wavelengths. The light may be moved in a raster pattern across groups of a sample, such as groups in columns and rows of the sample 120. Alternatively, the excitation light 105 may illuminate one or more entire regions of the sample 120 at one time and serially stop through the regions in a "step and shoot" scanning pattern. Line scanning can also be used as described, for example, in U.S. Pat. No. 7,329,860, of which the complete subject matter is incorporated herein by reference in its entirety. The sample 120 produces at least one of emission light 134 and transmission light 136 that is directed toward the lens 122. Emission light 134 may be generated in response to illumination of a fluorescent component in the sample 120 responsive to excitation source 104. Alternatively, the emission light 134 may be generated, without illumination, based entirely on emission properties of a material within the sample 120 (e.g., a radioactive or chemiluminescent component in the sample).

The transmission light 136 may result when the excitation source 104 directs excitation light 105 from a location above the sample 120 onto an upper surface of the sample 120 and the sample 120 reflects the transmission light 136. Alternatively, transmission light 136 may result when the excitation light 105 is located below the sample 120 and directs upward through the holder 118 through the sample 120. The transmission and emission light 136 and 134 may result from a common excitation light 105 or separate excitation lights 105. The emission light 134 and transmission light 136 are conveyed through the lens 122, along the optical assembly 106 and are directed onto corresponding code and label detectors 110 and 116.

In the example of FIG. 2, the emission light 134 and the transmission light 136 are separated at a beam splitter 141 along separate orthogonal optical paths 137 and 139. The emission light 134 may include label information produced by labels within the sample 120. The emission light 134 is conveyed along optical path 137 through the lens/filter assembly 114 onto the label detector 116. The transmission light 136 may include code information associated with optically detectable codes within or on the sample 120. The transmission light 136 may also include information associated with at least one of reflection or refraction of an optical substrate(s) (e.g., flow cell, sample holder, microparticles, and the like). The transmission light 136 is directed along optical path 139 through the lens/filter assembly 112 onto the code detector 110. Optionally, the code and label detectors 110 and 116 may be combined into a common detector to detect both emission light 134 and transmission light 136. Alternatively, the sample 120 may have only one of code information and label information therein. Thus, only the corresponding one of the label detector 116 and code detector 110 would be provided and utilized.

In some embodiments, the label information or signals from the emission light 134 includes first fluorescent signals emitted in response to a first excitation wavelength and also second fluorescent signals emitted in response to a second excitation wavelength. The first and second fluorescent emissions typically include light at different wavelengths. The first and second fluorescent signals may be emitted by, for example, a carboxyfluorescein (FAM) label and a near-infrared (NIR) label.

The optical assembly 106 may have different actual focal planes for the different spectral bands. For example, due to inherent properties, arrangement, or alignment of the focus components in an optical assembly, an optimal focal plane for detecting a first spectral band may be spaced apart or separated from an optimal focal plane of a second spectral band for the same optical assembly. However, the optical assembly may also be adapted to have different focal planes for different spectral bands. For example, the optical assembly 106 may be configured such that first and second light emissions are conveyed along different optical paths. The first and second light emissions may be conveyed to an objective lens located adjacent to the sample and along a common optical path therefrom. The first and second light emissions may then be filtered and/or reflected such that the first and second light emissions are directed along different optical paths and detected by different cameras or detectors. The focus components along the different optical paths may be arranged to form different focal planes. Accordingly, the focal plane of the optical assembly 106 for the first light emissions may be different than the focal plane of the optical assembly 106 for the second light emissions.

In alternative embodiments, the first and second light emissions are separately conveyed along generally the same optical path, but the focus components 108 or other components of the imaging subsystem 100 are adjusted to affect the degree of focus for the different light emissions. For example, in one embodiment, a first excitation wavelength is first incident upon the sample. The emission light 134 may include first fluorescent signals that are conveyed along an optical path. The emission light 134 may then be detected by a detector or camera. After excitation of the sample with the first excitation wavelength, the focus components 108, the sample holder 118, and/or other components of the imaging subsystem 100 are adjusted in a manner that moves the actual focal plane 119. The second excitation wavelength is incident upon the sample and the emission light 134 includes second fluorescent signals that are conveyed along the same optical path. The emission light 134 is then detected by the same camera or detector. However, the actual focal planes 119 associated with the first and second fluorescent emission signals are different.

The code and label detectors 110 and 116 and any other detectors of the imaging subsystem 100 may detect images from the sample 120. The label detector 116 may include multiple label detectors or cameras. Each image comprises an array of pixels, values for which are dependent upon the intensity of the light including corresponding code and label information. The information may also be associated with the reflection and/or refraction of light from an optical substrate. The images are representative of one or more regions into which the sample 120 has been apportioned during the imaging operation. The images detected at code and label detectors 110 and 116 or other detectors of the imaging subsystem 100 are passed to the computer 102. Each detected image has an associated degree of focus that corresponds to, and is dependent upon, the focal settings of the optical assembly 106.

The label and code detectors 116 and 110 may be, for example photodiodes or cameras. In some embodiments herein, the detection camera can comprise a 1 mega pixel CCD-based optical imaging system such as a 1002×1004 CCD camera with 8 µm pixels, which at 20× magnification can optionally image an area of 0.4×0.4 mm per tile using an excitation light 105 that has a laser spot size of 0.5×0.5 mm (e.g., a square spot, or a circle of 0.5 mm diameter, or an elliptical spot, etc.). The detection cameras can optionally have more or less than 1 million pixels, for example a 4 mega pixel camera can be used. In many embodiments, it is desired that the readout rate of the camera should be as fast as possible, for example the transfer rate can be 10 MHz or higher, for example 20 or 30 MHz. More pixels generally mean that a larger area of surface, and therefore more sequencing reactions or other optically detectable events, can be imaged simultaneously for a single exposure. In particular embodiments, the CCD camera/TIRF lasers may collect about 6400 images to interrogate 1600 tiles (since images are optionally done in 4 different colors per cycle using combinations of filters, dichroics and detectors as described herein). For a 1 Mega pixel CCD, certain images optionally can contain between about 5,000 to 50,000 randomly spaced unique nucleic acid clusters (i.e., images upon the flowcell surface). At an imaging rate of 2 seconds per tile for the four colors, and a density of 25000 clusters per tile, the systems herein can optionally quantify about 45 million features per hour. At a faster imaging rate, and higher cluster density, the imaging rate can be improved. For example, a readout rate of a 20 MHz camera, and a resolved cluster every 20 pixels, the readout can be 1 million clusters per second. A detector can be configured for Time Delay Integration (TDI) for example in line scanning embodiments as described, for example, in U.S. Pat. No. 7,329,860, of which the complete subject matter is incorporated herein by reference in its entirety.

The images detected at the code detector 110 are stored as code images 140 in code image sets 130 in memory 128. A code image set 130 stores code information (ID and position for) a sample 120 and comprises a series of code images 140 associated with the adjacent individual regions into which a sample 120 is apportioned (as explained below in more detail). The memory 128 also stores label image sets 132 that comprise label images 142 which are detected at the label detector 116. A label image set stores label information (type and position) for a sample 120. For example, for each type of label, the label image set 132 may comprise a series of label images 142 associated with adjacent individual regions of the sample 120. The label image set 132 may also include label images 142 for different labels (e.g., FAM, NIR) for reach region.

The computer 102 includes, among other things, an image analysis module 124, a focus control module 126, and the memory 128. The analysis module 124, among other things, analyzes images obtained at one or both of the code and label detectors 110 and 116 in order to identify the ID and type of labels and codes within the sample 120. The analysis module 124 also analyzes the images to obtain the position of the labels and codes within the sample 120. The images 140, 142 may contain an emission pattern and/or a transmission pattern produced by the sample 120 and output as the emission light 134 and/or transmission light 136. The analysis module 124 analyzes the emission pattern and/or transmission pattern to identify the ID, type, and position of codes and labels within the sample 120.

The analysis module 124 also analyzes the same code and label images 140 and 142 to determine a degree to which the optical assembly 106 is focused in a desirable manner on the sample 120. The analysis module 124 calculates a focus score associated with the code and/or label image(s) 140 and 142. The focus score represents the degree to which the optical assembly 106 was in focus when the code and label detectors 110, 116 captured the code and/or label image 140, 142. The analysis module 124 may calculate the focus score based on one or more image quality parameters. Examples of image quality parameters include image contrast, spot size, image signal to noise ratio, and the mean-square-error between pixels within the image. By way of example, when calculating a focus score, the analysis module 124 may calculate a coefficient of variation in contrast within the image. The coefficient of variation in contrast represents an amount of variation between intensities of the pixels in an image or a select portion of an image. As a further example, when calculating a focus score, the analysis module 124 may calculate the size of a spot derived from the image. The spot can be represented as a Gaussian spot and size can be measured as the full width half maximum (FWHM), in which case smaller spot size is typically correlated with improved focus. The image quality parameters are measured directly from the actual sample image(s) that are scanned and also analyzed to identify the codes and labels. The image quality parameters are not necessarily obtained from a separate dedicated focus image. The analysis module 124 continuously calculates real time image quality parameters to achieve the desired degree of focus. The computer 102 uses the image quality parameters in a control loop to maintain or lock the optical assembly 106 at the preferred focal plane 121.

Emission light 134 is captured in a label image 142 as a fluorescence spatial emission pattern. The analysis module 124 may calculate the focus score based on image quality parameters (e.g., contrast or spot size) of the fluorescence spatial emission pattern. Optionally, the sample 120 may comprise multiple microparticles that have one or more different labels that emit fluorescence at one or more different wavelengths. The label image 142 contains a fluorescence spatial emission pattern emitted by the different wavelengths associated with the labels. The analysis module 124 identifies the individual labels based on the fluorescence spatial emission pattern within the image. The analysis module 124 may perform both determination of the focus score and identification of the type and position of the labels from the single common label image 142. In some embodiments, the captured emission light 134 is limited to a spectral band. In such images where the fluorescence spatial emission pattern is known, the analysis module 124 may determine only the position of the labels in the label images 142.

Optionally, the sample 120 may comprise multiple microparticles that have optically detectable codes therein or thereon. The codes produce the transmission light 136 that is detected at the code detector 110 and stored in memory 128 as code images 140. The code detector 110 captures the codes in the code image 140 as a coded spatial transmission pattern. The analysis module 124 calculates the focus score based on image quality parameters (e.g., contrast or spot size) within the coded spatial transmission pattern. The microparticles within the sample 120 may have chemical probes attached thereto, where each of the chemical probes is associated with a corresponding one of the codes. The code image 140 captured by code detector 110, and containing the optically detectable codes spatially distributed there across, is then analyzed by the analysis module 124. The analysis module 124 identifies the codes, both for ID and position, from the same common code image 140 as used to obtain the focus score.

Furthermore, the transmission light 136 may include at least one of reflection and refraction information about the sample or about an optical substrate that holds the sample. For example, the transmission light 136 may include reflection and/or refraction information regarding a surface of a flow cell. The reflection and/or refraction information may be associated with microparticles that have the biomolecules immobilized thereon. The reflection and/or refraction information may be associated with a sample holder.

Figure 3:
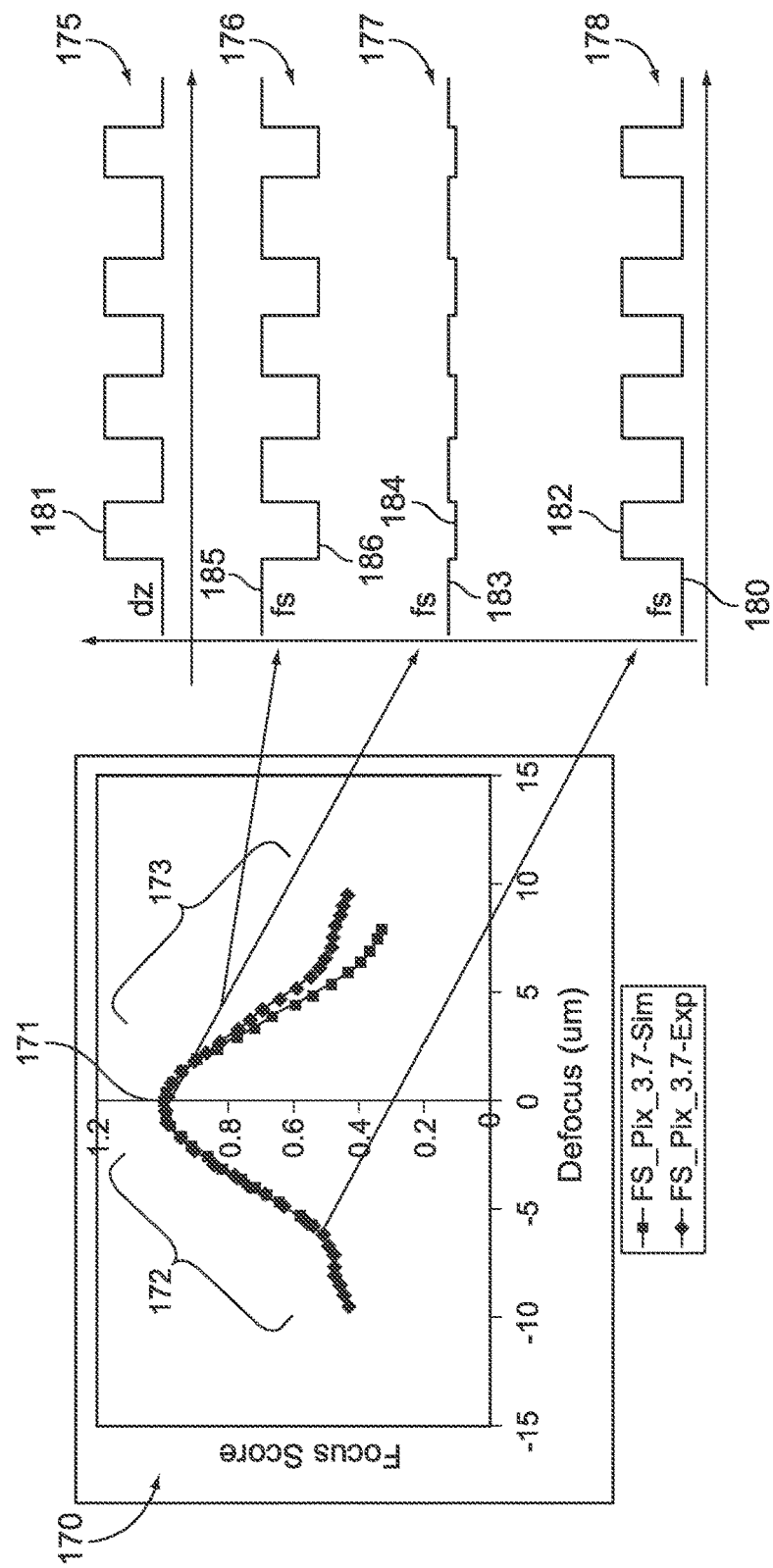
FIG. 3 illustrates a graph plotting a relation between the focus score and a defocus spread.

FIG. 3 illustrates a graph 170 plotting a relation between the focus score (on the vertical axis) and a defocus spread (along the horizontal axis). The focus score may correspond to the coefficient of variation in contrast, spot size, or another image quality parameter as discussed herein. The defocus spread, as shown at 123 in FIG. 2, represents a difference between the actual focal plane 119, to which the focus components 108 are set, and a preferred focal plane 121, at which images should be obtained with a preferred degree of focus.

The relation in graph 170 includes a local maximum 171 where the defocus spread approaches zero and the optical assembly 106 obtains images having the preferred degree of focus. At the local maximum 171, the actual focal plane 119 is co-located with the preferred focal plane 121. The actual focal plane 119 may be spaced from the preferred focal plane 121 by a positive or negative distance. For example, the actual focal plane 119 may be positioned −1 micrometers (μm), −5 μm, −10 μm, +1 μm, +2 μm, etc. from the preferred focal plane 121. In graph 170, the tail 172 represents the range of the defocus spread in which the actual focal plane 119 is moved in a negative direction from (e.g., below) the preferred focal plane 121. In graph 170, the tail 173 represents the range of the defocus spread in which the actual focal plane 119 is moved in a positive direction from (e.g., above) the preferred focal plane 121. As the defocus spread increases in the negative or positive direction, the focus score decreases in a predetermined manner represented by the graph 170. The graph 170 is merely illustrative. The shape of the graph will vary based upon the type and properties of the optical system, the properties of the sample, the content of the images, and the like.

In accordance with at least one embodiment, the focus control module 126 compares the current change in the focus score to the shift dz and to past focus scores in order to identify a direction and an amount to change the focal offset. To understand how the focus control module 126 may determine direction and amounts to adjust the focal offset, attention is directed to FIG. 3.

FIG. 3 also illustrates an exemplary shift dz plotted at 175 that may be introduced into the z-distance between the lens 122 and the sample 120. Below the shift dz 175, three alternative focus score plots 176-178 are presented. The focus score plots 176-178 illustrate alternative patterns that may be exhibited by the focus score in response to the shifts dz in the actual focal plane 119. The alternative focus score plots 176-178 are associated with three separate points along the graph 170. Plots 176-178 illustrate that, depending upon the state of the optical assembly 106 along the graph 170, the focus score will change by a different amount and with a different phase for each shift dz in the defocus spread.

Plot 178 provides an example of how the focus score may change when the state of the optical assembly 106 is in a low/poor degree of focus, such as where the defocus spread is −5 μm. In plot 178, the focus score begins (at 180) with a low/poor value corresponding to a defocus of −5 μm. The shift dz is added to the focus setting at 181. For example, the shift dz may be 0.5 μm. Thus, when the shift dz=0.5 μm is added to the z-distance of the optical assembly 106, the defocus spread is reduced to −4.5 μm. As the defocus spread is reduced, the focus score improves at 182. The transition (between 180 and 182) in the focus score (e.g., changing from a low value to a better value) is in phase with the shift dz to 181 which also changed from a low value to a better value.

Plot 176 provides an example of how the focus score may change when the state of the optical assembly 106 is in a low/poor degree of focus, such as where the defocus spread is +4 μm. In plot 176, the focus score begins (at 185) with a medium value corresponding to a defocus of 6 μm. The shift dz is added to the focus setting at 181. For example, the shift dz may be 0.5 μm. Thus, when the shift dz=0.5 μm is added to the z-distance of the optical assembly 106, the defocus spread is increased to 4.5 μm. As the defocus spread moves further away from zero, the focus score deteriorates or worsens at 186. The transition between 185 and 186 in the focus score, namely changing from a medium value to a low value, is 180 degrees out of phase with the shift dz to 181 which transitioned from a low value to a high value.

In connection with plots 176 and 178, the focus control module 126 analyzes the phase of each change in the focus score relative to the phase of the shift dz to make a determination regarding whether the defocus spread is positive or negative. For example, when the change in focus score is in phase with the shift dz, then the defocus spread is positive. Alternatively, when the change in the focus score is out of phase with the shift dz, then the defocus spread is negative. Once the sign of the defocus spread is determined, the focus control module 126 determines whether to adjust the focus setting by increasing or decreasing the z-distance 138. Thus, the phase relation of the focus score and defocus spread is utilized to determine a direction in which to adjust the focus setting.

Plot 177 provides an example of how the focus score may change when the state of the optical assembly 106 is already in a high/good degree of focus, such as where the defocus spread is near or at 0 μm. In plot 177, the focus score begins (at 183) with a high/good value corresponding to a defocus of 0 μm. The shift dz is added to the focus setting at 181. When the shift dz=0.5 μm is added to the z-distance of the optical assembly 106, the defocus spread is increased to 0.5 μm. As the defocus spread moves slightly away from zero, the focus score deteriorates or worsens slightly at 184. The transition between 183 and 184 in the focus score is 180 degrees out of phase with the shift dz transition to 181.

In connection with plot 177, the focus control module 126 analyzes the amplitude of the change in the focus score for one step in the shift dz to make a determination regarding whether the defocus spread is near or far from a preferred focus value (e.g., zero). For example, when the change in focus score for one step in the shift dz is small, then the defocus spread is small. Alternatively, when the change in the focus score is large for one step in the shift, then the defocus spread is large. Once the amplitude of the defocus spread is determined, the focus control module 126 determines an amount of the adjustment to the focus setting. Thus, the amplitude and phase of the transition in the focus score is utilized to determine an amount and direction to adjust the focus setting.

Figure 4:
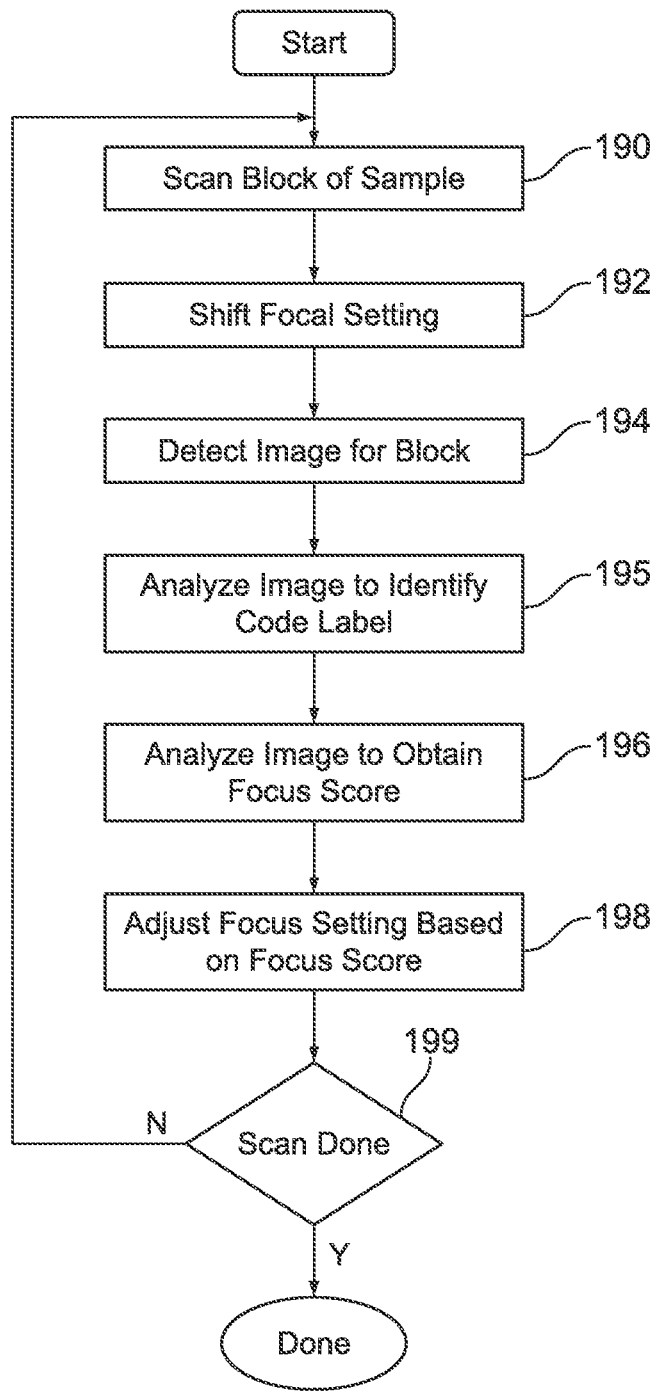
FIG. 4 illustrates a method for controlling focus dynamically of an optical imaging system in accordance with an embodiment.

FIG. 4 illustrates a method for controlling focus dynamically for an optical imager in accordance with an embodiment. At 190, a sample is scanned with the optical assembly 106 that apportions the sample 120 into regions based on a scan pattern. The optical assembly 106 has a focal setting with respect to the sample 120. As illustrated in FIG. 2, the regions may be arranged adjacent to one another in a non-overlapping manner.

At 192, the focal setting of the optical assembly 106 is shifted during scanning of the sample 120. The shifting operation may include modulating a z-position of the focus lens repeatedly with respect to the sample 120. The shifting operation may include periodically adding a focal offset (e.g., a dz) to the focal setting. The shifting operation introduces an error signal into a focal position of the optical assembly. The error signal is monitored as a function of the focal position of the optical assembly. By way of example only, the optical path length (e.g., z-distance 138) may be modulated by 0.5 µm every 5 µm of physical scan distance in the x direction across the sample. The shift may be introduced at a predetermined periodic rate (e.g., 125 Hz, 12.5 Hz, and the like). For example, it may be desirable to vary the shift at 125 Hz. Thus, the focus control module 126 introduces the shift every 10 scan lines (e.g., columns) and maintains the shift for 10 scan lines before removing the shift for 10 scan lines. Columns in a region may be scanned at a rate of 1.25 mm/sec with 0.5 µm resolution. Alternatively, it may be desirable to vary the shift at 12.5 Hz. Thus, the focus control module 126 introduces the shift every 100 scan lines (e.g., columns) and maintains the shift for 100 scan lines before removing the shift for 100 scan lines.

At 194, the system detects one or more images representative of one of the regions from the sample 120. The image(s) has an associated degree of focus corresponding to the focal setting of the optical assembly 106. The image(s) may contain at least one of an emission pattern and a transmission pattern produced by the sample 120. At 195 the system identifies emission and/or transmission patterns. For example, a region may have a width of 10 columns or scan lines, a width of 100 columns or scan lines, a width of 5 µm, 20 µm and the like.

At 196, the system analyzes the one or more images to obtain the focus score or scores corresponding thereto. The analyzing operation calculates the focus score(s) based on at least one of contrast, spot size, a signal-to-noise ratio, and a mean-square-error between pixel values for the at least one image being analyzed. The analyzing operation includes calculating a coefficient of variation in contrast for the image, the coefficients of variation in contrast representing the focus score. As a further example, the analyzing operation can include calculating the size of a spot derived from the image. The spot can be represented as a Gaussian spot and the full width half maximum (FWHM) can represent the focus score. The identifying operation at 195 and the analyzing operation at 196 operate upon the same image to identify the focus score and the emission and/or transmission patterns. When the sample emits fluorescence that is captured in the image as a fluorescence spatial emission pattern, the focus score can be based on contrast or spot size within the fluorescence spatial emission pattern. When the sample has at least one of first and second labels that emit fluorescence at different first and second wavelengths, the variation in contrast or spot size may be calculated for only one or for both of the first and second wavelengths. The system detects the first and second labels from the same image utilized to obtain the focus score.

At 198, the focus control module 126 adjusts the focus setting based on the focus score or focus scores. As part of the adjustment operation, the amplitude and phase of the focus score is analyzed. It is determined whether the focus score is in phase, or out of phase, with the shift. It is also determined whether the focus score changed by a large amount or a small amount during the most recent shift. Based on the phase and amplitude changes of the focus score, the focus control module 126 determines a direction and an amount to change the focus shift. The adjusting operation reduces the error signal by adjusting the focal position. By way of example, the focal setting at 198 may be calculated using a PI ("proportional/integral") feedback loop. The focus score is first calculated using the following equation (1):

$$CV(y_i) = \frac{\sigma(y_i; z)}{\mu(y_i; z)}$$

In the equation (1), the focus score is calculated for an image at a particular z distance. The variable $y_i$ represents pixel values along the y-axis for a given z-distance. The focus score equals the ratio of the standard deviation for the variable $y_i$ over the mean for the variable $y_i$ for a current group in the image. The CV is integrated over $N_{COL}$ columns 9 or other groups) for an entire image. Once the CV value is known for the image, an error signal can be calculated based on equation (2) below:

$$e(y_i) = \frac{[CV(y_i; z + dz) - CV(y_{i-1}; z)]}{N_{col}}$$

The error signal $e(y_i)$ in equation (2) represents a difference between the CV value for the current group $y_i$ and the CV value for the next group $y_{i-1}$. Once the error signal $e(y_i)$ is known, the correction to the focus offset may be chosen based on the following equation (3):

$$\Delta z_{i+i} = g_P e(y_i) + g_I \sum_{j=i-N}^{i} e(y_i)$$

In equation (3), "$g_p$" and "$g_I$" represent gain factors, while "$e(y_i)$" represents a proportion, and "$\Sigma e(y_i)$" represents an integral. The shifting, analyzing, and adjusting operations are continuously updated during a time delay integration scan using real time information in the image to control a focal position of the optical assembly. The shifting, analyzing, and adjusting operations are continuously repeated in a control loop to lock in on a desired focal position of the optical assembly.

Optionally, the amount of correction made at each iteration through 190-198 in FIG. 4 may be limited to a maximum incremental change in focus offset. This limitation may be the same or different for various regions as the imaging system steps across the sample. At 199, the process determines whether the current region is the last region on a sample. When the currently scanned region is the last region, the process is done. When the currently scanned region is not the last region, flow returns to the beginning above 190 and the next region is scanned.

Figure 5:
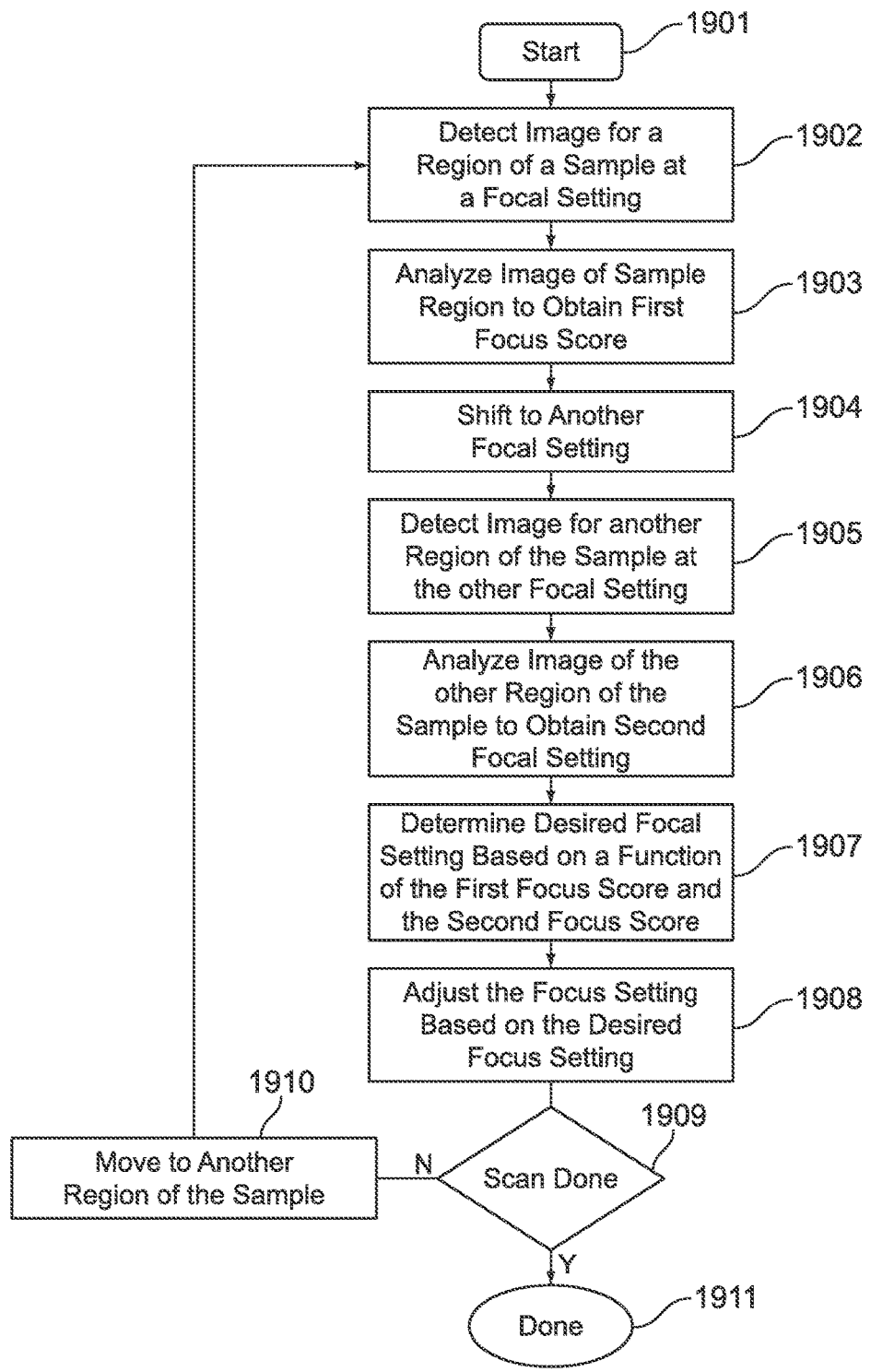
FIG. 5 illustrates a further embodiment for controlling focus dynamically of an optical imaging system.

FIG. 5 illustrates a method in accordance with another embodiment of the invention. At 1901, a method for controlling focus dynamically for an optical imager is initiated. At 1902 an image for a region of a sample is obtained with the optical assembly 106. The optical assembly 106 has a focal setting with respect to the sample 120. As illustrated in FIG. 2, the regions may be arranged adjacent to one another in a non-overlapping manner.

At 1903, the image of the region obtained in 1902 is analyzed to obtain a first focus score. The analyzing operation calculates the focus score, for example using methods set forth above in regard to 195 of FIG. 4. Thus, focus score can be based on at least one of contrast, spot size, a signal-to-noise ratio, and a mean-square-error between pixel values for the at least one image being analyzed. The analyzing operation can include calculating a coefficient of variation in contrast for the image, the coefficients of variation in contrast representing the focus score, or the analyzing operation can include calculating the size of a spot derived from the image.

At 1904 the focal setting of the optical assembly 106 is shifted. The shifting operation may be carried out as set forth above in regard to 192 of FIG. 4. Thus, shifting can include modulating a z-position of the focus lens with respect to the sample 120. The shifting operation may include adding a focal offset (e.g., a dz) to the focal setting to a known or predetermined extent. The extent of the shift can be characterized in terms of magnitude, such as the size of dz, and direction, such as the sign (+/−) of dz. The extent of the offset can be determined at any step prior to 1904 including for example, prior to 1903, 1902 or 1901. The shifting operation introduces an error signal into a focal position of the optical assembly. The error signal can be monitored as a function of the focal position of the optical assembly as set forth below in the context of the following steps.

At 1905, the system obtains an image representative of a second region from the sample 120 at the focal setting to which the optical assembly was shifted in 1904. The image has an associated degree of focus corresponding to the focal setting of the optical assembly 106. The image may contain at least one of an emission pattern and a transmission pattern produced by the sample 120. Returning to the example of FIG. 2, the second region can be adjacent to or overlapping with the region that was imaged at 1902.

At 1906 the image of the region obtained in 1905 is analyzed to obtain a second focus score. The analyzing operation is carried out as set forth above in regard to 1903 and a focus score of a similar type is obtained.

At 1907, a desired focal setting is determined based on a function of the first focus score and the second focus score. For example, the amplitude and phase of the focus scores can be analyzed. Thus, it can be determined whether the difference in the first focus score determined at 1903 and the second focus score determined at 1906 is in phase, or out of phase, with the shift at 1904. It can also be determined whether the focus score changed by a large amount or a small amount as a result of the shift. By way of example, the desired focal setting may be calculated using a PI ("proportional/integral") feedback loop. The focus score is first calculated using equations (1), (2) and (3) as set forth above in regard to 198 of FIG. 4.

In some embodiments, the desired focal setting may be determined based on multiple focus scores for each focal setting. For example, steps 1902-1906 may be repeated one or more times to obtain a plurality of first focus scores corresponding to one focal setting and a plurality of second focus scores corresponding to another focal setting. The plurality of first, focus scores may be determined from different images along the scan region, and the plurality of second focus scores may be determined from different images along the scan region. More specifically, the optical assembly 106 may alternate between first and second focal settings as the optical assembly moves along the scan region and obtain a plurality of focus scores for each focal setting. The determining, at 1907, may be based on at least one of a function of the first focus scores and a function of the second focus scores. For example, the determining operation may be based on a function of an average of the first focus scores and an average of the second focus scores.

At 1908 the focal setting is adjusted based on the desired focal setting. The focus control module 126 adjusts the focus setting based on the focus desired focal setting. The desired focal setting can be communicated to the focus control module as a particular setting or as an extent of change from a current or otherwise known focal setting. For example, based on the phase and amplitude changes of the focus score, the focus control module 126 can determine a direction and an amount to change the focus shift. The adjusting operation will typically reduce the error signal by adjusting the focal position. It is possible that the desired focal setting is the same as the current focal setting and little to no change is necessary or desired. In such a situation the focus control module can be instructed to make little or no change to the current focal setting.

At 1909, the process determines whether the current region is the last region on a sample for which an image is desired. When the currently scanned region is the last region, the process is done 1911. When the currently scanned region is not the last region, the system proceeds to 1910 where the relative location of the optical assembly and the sample is changed such that another region of the sample is positioned for imaging. Flow then returns to 1902 and the other region is scanned.

FIG. 6 illustrates a graphical representation of a dynamic focus control operation that may be carried out by the imaging subsystem 100 of FIG. 2 in connection with the method of FIGS. 4 and 5. In FIG. 6, a top plan view of a first portion of the sample 120 is shown, such as from the view point of the lens 122 of FIG. 2. A series of regions 152 are overlaid on the sample 120 to demonstrate a potential step-wise scan pattern that apportions the sample 120. Separate images are captured for each region 152 of the sample 120. In the example of FIG. 6, the sample 120 is comprised of an array of micro-particles 154 arranged in groups such as rows and columns. When an excitation source 104 (FIG. 2) is used, a light source 104 may be controlled to move in a raster scan pattern along each column of the region 152. The raster motion may be achieved by moving the light source 104 with respect to the sample 120, or by moving the holder 118 in the x and y directions. The raster scan pattern may move from top to bottom downward, or from bottom to top upward, along each column. As a column is scanned by the light source 104, a corresponding column of the image is captured at detectors 110, 116. Once a column is scanned (and the corresponding column of the image is captured), the light source may be moved to the next column and the process repeated for consecutive columns until an image is captured for the entire region 152.

Optionally, multiple groups may be scanned in one pass (at the same time). As a further option, an entire region 152 may be scanned by the light source in one pass from top to bottom, or bottom to top. As yet a further option, each region 152 need not be illuminated with a moving light source. Instead, a complete region 152 may be illuminated at once by the light source and the image obtained for the entire region 152 instantaneously as a snap-shot to capture an image associated with the region 152 at one point in time. After the image is captured for the first region 152, the process is repeated for the second region 152 in a step and shoot manner. With each of the foregoing techniques for capturing an image for one region 152, the overall sample 120 is "scanned" by repeating the capture process sequentially for multiple regions 152, regardless of whether the excitation light 105 is moved relative to a current region, rastering or otherwise.

In FIG. 6, the regions 152 are labeled A-E for purposes of illustration. The sample 120 is apportioned such that regions A-E are arranged in a non-overlapping manner. When images are captured for each of the regions A-E, the images form a series of adjacent images that are separate and distinct from one another. In the example of FIG. 6, an image set 156 is shown to include images A-E which correspond to the regions A-E from the sample 120. The analysis module 124 (FIG. 2) analyzes one or more of the images A-E to identify and locate codes and/or labels, and to calculate values for image quality parameters associated with the focus score. The analysis module 124 (FIG. 2) may also analyze one or more of the images A-E to identify and locate areas of reflection and/or refraction and calculate corresponding values for image quality parameters.

FIG. 6 also illustrates a series of graphs 160-163 that are referenced in connection with explaining an application of the focus control process implemented in accordance with at least one embodiment. The horizontal axis in each graph corresponds to the x-position across the bottom 155 of the sample 120. In graph 160, the vertical axis corresponds to the z-distance 138 (FIG. 2) between the lens 122 and the preferred focal plane 121 of the sample 120. Graph 160 plots an example of how the focus control module 126 may adjust the distance between the focus lens 122 and the sample 120 as a scan steps across the sample 120.

In graph 161, the vertical axis represents the degree of focus for each image. Graph 161 plots an example of how the degree of focus changes from the first region A to the last region E during a scanning process. In graph 162, the vertical axis represents an image quality parameter, such as coefficient of variation (CV) that is calculated by the analysis module 124 for images A-E. Graph 162 plots exemplary CV values calculated by the analysis module 124 for each of images A-E. In graph 163, the vertical axis represents a shift that is introduced by the focus control module 126 into the z-distance 138. Graph 163 plots a series of focal offsets that are periodically added. It should be recognized that FIG. 6 is illustrative only and that the sizes, inter-relation, and number of focal offsets, CV calculations, and changes in the focus setting and degree of focus are narrative, not actual.

First, the region A is scanned. During capture of at least a first portion (e.g., one or more of the columns) of the first image A for region A, the optical assembly 106 has an initial focal setting. For example, the initial focal setting may be set to a z-distance 138 that is denoted at focal setting Az in graph 160. During the scan of region A, the focus control module 126 introduces at least one temporary shift (as denoted at shift Adz) into the focal setting Az of the optical assembly 106. For purposes of simplification, the focus process is described in connection with one shift during scan of a complete region. However, it should be recognized that multiple shifts may be performed during scan of a single region and a corresponding number of multiple adjustments to the focal setting may be made during scan of the same region.

During the scan of region A, the lens 122 is located a z-distance 138 from the sample 120 that is determined by the focal setting Az and in addition by the shift Adz. The label and/or code detectors 116, 110 detect an image A, representative of region A. The image A has an associated degree of focus corresponding to the focal setting Az and shift Adz. The analysis module 126 analyzes the image A to obtain the focus score CVa. The focus score CVa represents a coefficient of variation in the contrast of the pixels in image A. Next, the focus control module 126 adjusts the focus setting based on the focus score as discussed above in connection with FIGS. 3 and 4. In the example of FIG. 6, the focus setting is adjusted to Bz (graph 160). During the scan of region B, the lens 122 is located a z-distance 138 from the sample 120 determined by the focal setting Bz. The shift Bdz is introduced during scan of region B and, once image B is captured, the focus score CVb is determined. Based on focus score CVb, the focal setting is adjusted to Cz. The process is repeated for regions C, D, and E, utilizing shifts Cdz, Ddz, and Edz. Focus scores CVc, CVd and CVe are calculated by the analysis module 124 and used to adjust the focal setting to Cz, Dz, and Ez. As shown in graph 161, the degree of focus improves/increases as the scanning process steps across the sample 120. Hence, the image E will have a higher degree of focus than the image A. The system can return to obtain an image of region A at a focal setting determined from the image of region E. However, the system need not return to scan a previous region that was obtained at a lower degree of focus. Rather, the region having a lower degree of focus can be ignored or discarded when evaluating the image of the sample.

Figure 7:
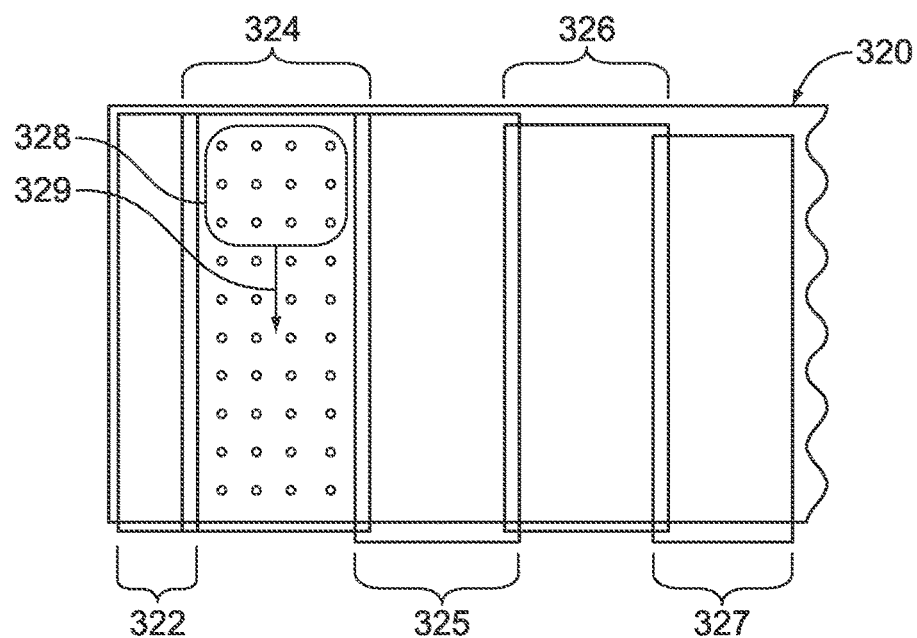
FIG. 7 illustrates an alternative scan arrangement of regions that may be scanned in accordance with an embodiment.

FIG. 7 illustrates an alternative scan arrangement for regions that may be obtained at 190 in FIG. 4 in accordance with an embodiment. In FIG. 7, a portion of a sample 320 is illustrated with a lead-in sub-region 322 that is scanned to obtain a reference focus score. For example, the sub-region 322 may be smaller (e.g., have less width) than the following regions 324-327. An excitation light 105 illuminates a beam spot 328 that is moved in the direction of arrow 329 to scan region 324. Optionally, the beam spot 328 may be smaller to cover fewer groups or columns of the region 324. The sub-region 322 is imaged and analyzed to obtain a focus score which is then used to adjust the focus offset. The regions 324-327 are arranged in an overlapping arrangement. For example, the overlap may correspond to one a few groups or columns.

Figure 8:
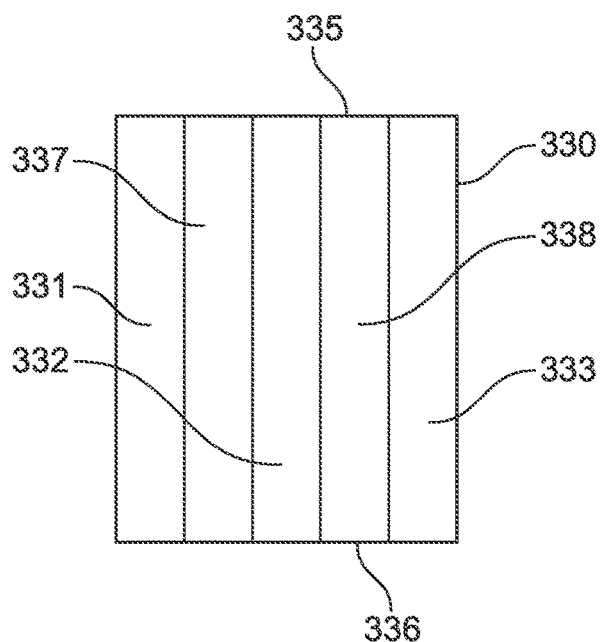
FIG. 8 illustrates an alternative arrangement in which the focus score may be obtained.

FIG. 8 illustrates an alternative arrangement in which the focus score may be obtained at 196 in FIG. 4. FIG. 8 illustrates an example of an image 330 that is obtained for a region of a sample. The image 330 is analyzed by the analysis module 124 to identify codes and labels as explained above. A subset of the columns in of the image 330 is also analyzed to obtain the focus score. For example, a portion of the image 330 may be designated as focal test regions 331-333. In the example of FIG. 8, the focal test regions 331-333 are defined as elongated strips that extend from the top 335 to the bottom 336 of the image 330 and are spaced apart from one another. The regions 337 and 338 between the focal test regions 331-333 are not analyzed to obtain focus scores. By using spatially distributed focal test regions 331-333, the system reduces the number of columns to analyze in each image 330 to obtain a focus score.

Figure 9:
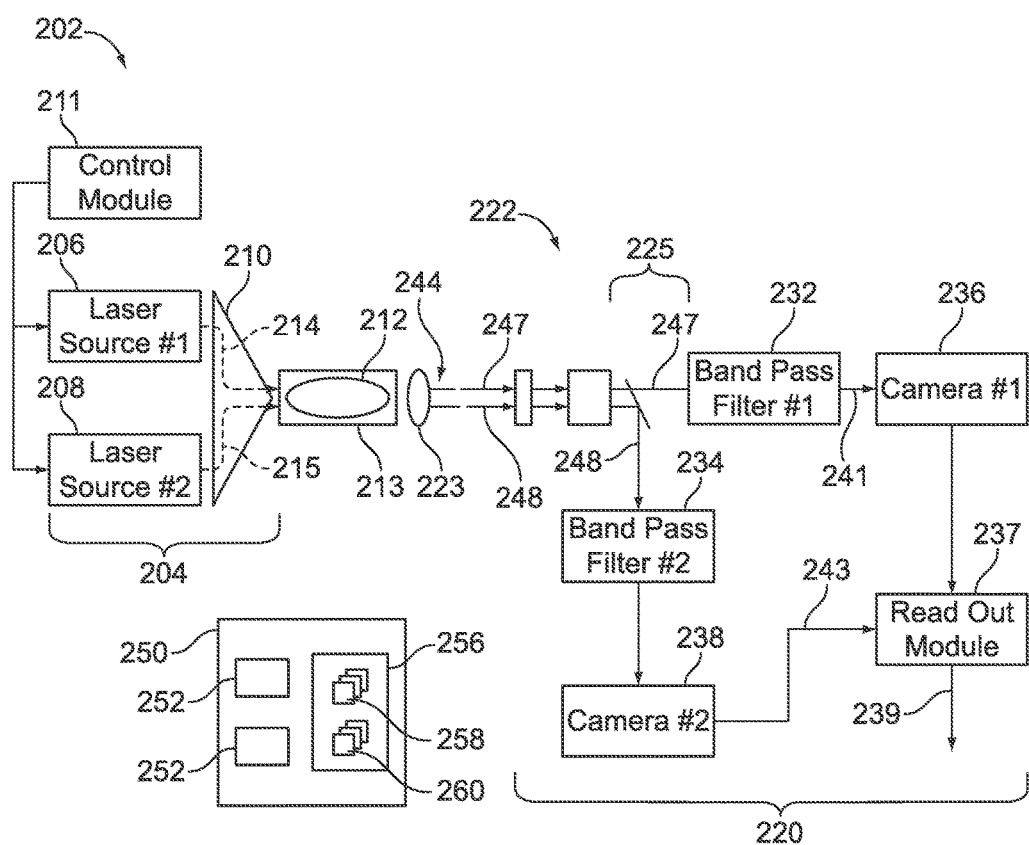
FIG. 9 illustrates an imaging system that is formed in accordance with an alternative embodiment.

FIG. 9 illustrates an imaging subsystem system 202 that is formed in accordance with an alternative embodiment. The subsystem 202 generally includes an excitation assembly 204, and a detection assembly 220. The excitation assembly 204 is optically coupled to a sample 212 that is, in turn, optically coupled to the detection assembly 220. The sample 212 is provided on a substrate 213. For example, the sample 212 may represent a plurality of nucleic acid clusters/beads or other features, with multiple fluorescent labels, which are attached to a surface of the substrate 213 (e.g., a flow cell or microarray). The excitation assembly 204 illuminates the same or common active area, or tile, in a temporally multiplexed manner with one or more different excitation wavelengths during successive excitation events. The excitation assembly 204 performs temporal multiplexing by generating one or more excitation wavelengths sequentially, such as through the use of multiple alternating sources or lasers 206 and 208, or multiple exposures of the same lasers. The lasers 206 and 208 are coupled through an excitation light guide 210 to illuminate a common area, or tile, on the substrate 213 and sample 212. In response thereto, the sample 212 emits fluorescence which is collected by an objective lens 223.

In the example of FIG. 9, a dashed line generally denoted at 214 illustrates an excitation beam that is channeled from the laser 206, through the light guide 210 and onto the sample 212 at a desired angle of incidence with respect to the surface or a reference plane on or within the substrate 213 holding the sample 212. A dashed line generally denoted at 215 illustrates an excitation beam that is channeled from the laser 208, through the light guide 210 and onto the sample 212 at a desired angle of incidence with respect to the surface or a reference plane on or within the substrate holding the sample 212. The control module 211 controls the excitation assembly 204 to generate an excitation light pattern. By way of example, the control module 211 may instruct the lasers 206 and 208 to generate excitation light at successive, non-overlapping periods of time. The laser 206 may supply a first pulse or burst of light as excitation beam 214 (e.g., at 532 nm) for a predetermined pulse duration, terminate the excitation beam 214, after which the laser 208 may supply a second pulse or burst of light as excitation beam 215 for a pulse duration and then terminate the excitation beam 215. In order to record two fluorophores with different wavelength emissions, each laser may be used once, or more than once on a single area (tile). For example, the sequence to record four different images in a single substrate tile may be a: wavelength one; filter one, b: wavelength one; filter two; c: wavelength two; filter three; d: wavelength two: filter four. The exposure time may be the same for each wavelength emission channel, or may be altered to control the intensity of the fluorescent signal recorded in the different channels. The exposure time may be the same for every cycle of sequencing, or may be increased throughout the sequencing run to compensate for any diminishing of the signal intensity as the cycles are performed.

The lasers 206 and 208 generate excitation light at different wavelengths that are chosen based on the wavelength spectrum of the fluorescent bases of interest that will potentially be present in the sample 212. In general, a number of bases may be labeled with a plurality of dyes or combinations of dyes, where each dye emits a corresponding known unique spectral pattern when illuminated with excitation light at a predetermined wavelength. For example, a number of bases (e.g., one or more) may be used that are each labeled with one or more dyes, where the dyes produce spectral patterns that are separately distinguishable along the wavelength spectrum. In a particular embodiment of the invention, each of the four bases is labeled with an individual fluorophore, such that the four bases can be spectrally distinguished, for example as described in PCT/GB2007/01770 or Bentley et al, supra (2008), the contents of which are incorporated herein by reference in their entirety.

The emission light 244 (e.g., fluorescence, luminescence, chemiluminescence, etc.) is generated at the sample 212, such as in response to the excitation beams 214 and 215, or in response to a chemical reaction when no excitation beams are used. The emission light 244 is comprised of multiple spectral bands denoted at 247-248. The spectral bands 247-248 generally differ from one another and may have different center wavelengths, mean wavelengths, median wavelengths, band widths, shapes, and the like. The detection assembly 220 is located downstream. The detection assembly 220 provides full field of view detection for the entire area of each tile of the substrate 213 measured by the objective lens 223.

The detection assembly 220 includes a dichroic member 225, band pass filters 232 and 234, detection cameras 236 and 238, a read out module 237 and a computer 250. The detection assembly 220 may include additional focus components that are not shown in FIG. 9. The detection assembly 220 is constructed entirely of non-moving parts that remain stationary and fixed with respect to one another, with respect to an axis of the optical system from the objective lens 223, and with respect to reflective and transmissive detection paths of the spectral bands 248 and 247, respectively. Accordingly, the detection or optical paths for the spectral bands 248 and 247 may be different. In some embodiments, the focal plane of the spectral bands 248 and 247 are also different.

The band pass filters 232 and 234 block high and low spectral content of the incoming spectral bands 247 and 248, respectively, and pass the portions of the spectral bands 247 and 248 within the upper and lower limits of the pass bands. The limits of the pass bands may be set to sharpen edges of spectral patterns, block noise, block scatter, block excitation light, and the like. The passed portions of the spectral bands 247 and 248 are directed onto corresponding detection cameras 236 and 238. The band pass filters 232 and 234, and detection cameras 236 and 238 may be oriented at various angles of incidence with respect to the transmissive and reflective paths and with respect to one another. For example, the detection cameras 236 and 238 may be oriented in a perpendicular geometry or acute angular relation with one another (e.g., 90°, etc.).

The detection cameras 236 and 238 detect the spectral bands 247 and 248, respectively, and provide electrical detection signals 241 and 243 to a readout module 237 to form images. The electrical detection signals 241 and 243 may be analog or digital signals representing an amount of emission energy (fluorescent or otherwise) measured by the detection cameras 236 and 238. The detection cameras 236 and 238 may output the detection signals 241 and 243 as continuous signals representative of an instantaneous measurement. The readout module 237 records the detection signals 241 and 243 and provides a series of images 239 representative of the emission light that was detected by each of the detection cameras 236 and 238. The readout module 237 passes the images to the computer 250.

The computer 250 includes an image analysis module 252, a focus control module 254, and memory 256. The memory 256 stores the images 258 and 260 captured by the detection cameras 236 and 238. The analysis module 252 and the focus control module 254 perform the shifting, analyzing and adjusting operations discussed above in connection with the embodiment of FIGS. 2-6.

Figure 10:
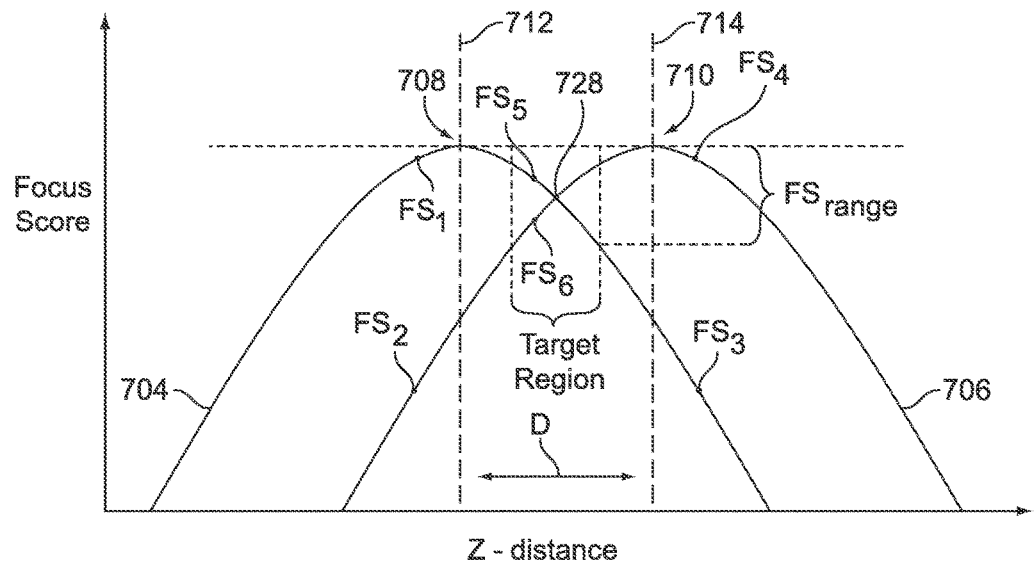
FIG. 10 illustrates a graph plotting relations between focus scores that are associated with light signals of two different spectral bands.
Figure 11:
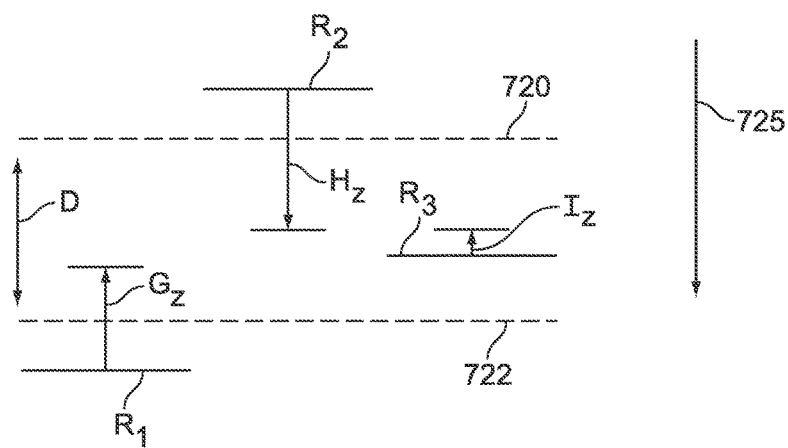
FIG. 11 illustrates a graphical representation of a dynamic focus control operation in accordance with various embodiments.
Figure 12:
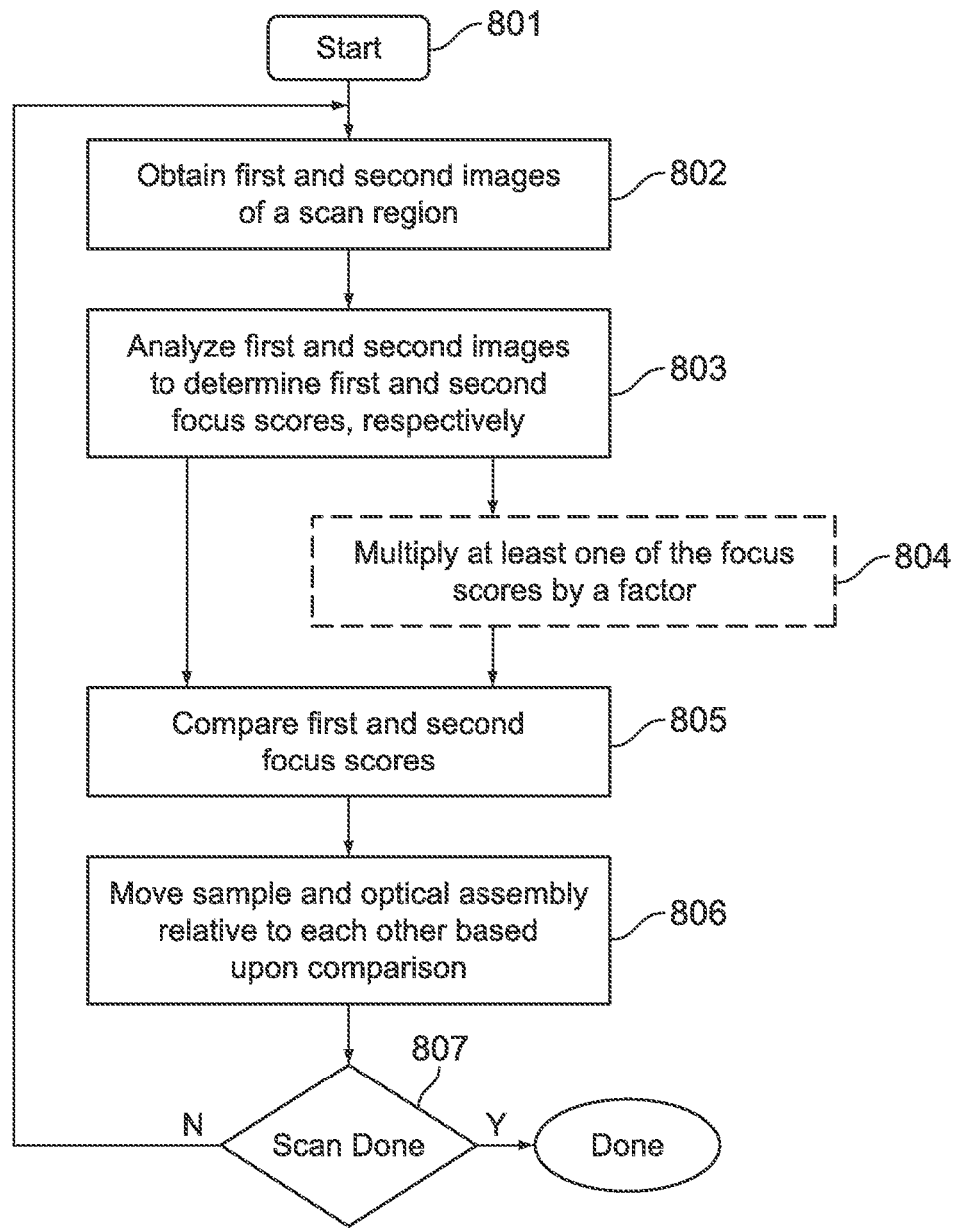
FIG. 12 is a block diagram illustrating a further embodiment for controlling focus dynamically of an optical imaging system.

FIGS. 10-12 illustrate another method for dynamically controlling a focus of an optical assembly or imaging subsystem using focus scores from different images. Embodiments described herein include obtaining images of detected light emissions from different labels to control focus dynamically. For example, FIG. 10 illustrates a graph 702 that plots focus-score curves 704 and 706 for first and second spectral bands, respectively. The optical assembly of the imaging subsystem may have different focal planes for detecting different labels as described above. The first spectral band may be associated with a first label (e.g., FAM-type label), and the second spectral band may be associated with a second label (e.g., NIR-type label). The first and second spectral bands may be different. Curve 704 shows the relation between the focus score and defocus spread of the first label. Curve 706 shows the relation between the focus score and defocus spread of the second label.

As shown in FIG. 10, the curves 704 and 706 have different local maxima 708 and 710, respectively. The local maxima 708 and 710 have vertical axes 712 and 714 extending therethrough. The vertical axes 712 and 714 may indicate where actual or optimal focal planes for the corresponding labels are located for an optical assembly of the imaging subsystem. Accordingly, the first and second spectral bands are detected with a higher degree of focus at different focal planes. The local maxima 708 and 710 (or the vertical axes 712 and 714) may be separated from each other by a distance D. The distance D represents the separation or spacing between the focal planes of the respective labels for the optical assembly. The distance D may be similar to a focal offset or shift dz as described elsewhere.

Also shown in FIG. 10, the local maxima 708 and 710 have approximately equal maximum focus scores $FS_{MAX}$. However, in some embodiments, the curves 704 and 706 may not have approximately equal maximum focus scores $FS_{MAX}$. In such embodiments, the focus scores may be multiplied by a factor so that the maximum focus scores $FS_{MAX}$ of the curves 704 and 706 are approximately equal.

The curves 704 and 706 intersect each other at an intersection point 728. A location of the intersection point 728 is based upon a shape of the curves 704 and 706, but is generally located at approximately half-way between the vertical axes 712 and 714 along the independent axis within a target region. The target region may represent a range of acceptable z-positions of the sample relative to the optical assembly. Furthermore, the intersection point is generally located within a desired focus score range $FS_{RANGE}$. As will be described in greater detail below, the imaging subsystem may control the focus so that the focus scores for different images are about within the desired focus score range $FS_{RANGE}$. For example, the imaging subsystem may move the z-position of the sample so that focus scores are within the target region. The imaging subsystem may also move the optical assembly relative to the sample so that the focus scores are within the target region.

The desired focus score range $FS_{RANGE}$ and the target region may be configured differently for different analysis protocols. In some embodiments, the desired focus score range $FS_{RANGE}$ is sufficient to enable the analysis module to determine what local areas in a flow cell or microarray interacted with a reagent or analyte and, optionally, to what degree. In other embodiments, the desired focus score range $FS_{RANGE}$ is generally sufficient to enable the analysis module to determine which microbeads interacted with a target analyte and, optionally, to what degree. In the illustrated embodiment, the desired focus score range $FS_{RANGE}$ may be something less than the maximum focus scores $FS_{MAX}$ associated with the first and second labels.

FIG. 11 shows an exemplary situation that may be encountered by an imaging subsystem when scanning a sample for different light signals, such as the emission signals associated with different first and second labels. In the exemplary embodiment, a common region R is scanned for light emissions from first and second labels in the sample. The dashed lines in FIG. 11 indicate focal planes 720 and 722 of the different labels for the optical assembly of the imaging subsystem. The focal planes 720 and 722 are separated by the distance D. The solid lines of the regions R in FIG. 11 represent a relative position of the sample regions with respect to the focal planes 720 and 722.

After the region R is scanned to detect the images, a focus score of each image is determined. In the exemplary embodiment, the images of the first and second labels are acquired simultaneously. However, the images may also be obtained sequentially. The focus scores of the two images may be analyzed (e.g., compared) to determine how to change or adjust the focal settings to dynamically control the focus of the system. Changing or adjusting a focal setting of the imaging subsystem includes relatively moving the sample along the viewing axis 725 by moving the sample or moving the optical assembly. Changing the focal setting of the imaging subsystem may also include moving or reconfiguring the focus components of the optical assembly to change the actual focal plane(s).

By way of example and with respect to FIG. 11, a first region $R_1$ may be excited by light sources (e.g., lasers) configured to excite the first and second labels within the sample. After excitation, the imaging subsystem scans the region $R_1$ of the sample and obtains first and second images relating to the first and second labels, respectively. The imaging subsystem determines focus scores for each of the first and second images of the scanned region $R_1$. The focus scores may correspond to the coefficient of variation in contrast, spot size, or another image quality parameter as described herein. The focus score associated with the first label is indicated in FIG. 10 as $FS_1$ and is located about within the desired focus score range $FS_{RANGE}$. The focus score associated with the second label is indicated in FIG. 10 as $FS_2$ and is not located about within the desired focus score range $FS_{RANGE}$.

After obtaining the focus scores $FS_1$ and $FS_2$ of images corresponding to the different labels, the imaging subsystem may analyze the focus scores $FS_1$ and $FS_2$. For example, the imaging subsystem may compare the focus scores and determine which focus score is greater than (or less than) the other and to what degree. As shown in FIG. 10, if the focus score $FS_1$ for the first label is greater than the focus score $FS_2$ for the second label, then the sample is located to the left of the target region (e.g., below the target region). The imaging subsystem may also determine a difference in the focus scores $FS_1$ and $FS_2$. The sample and/or optical assembly may be moved relative to each other so that the sample is moved closer to the target region between the focal planes 720 and 722. The amount of movement may be based upon the difference between the focus scores $FS_1$ and $FS_2$. For example, the sample may be moved a shift Gz along the viewing axis 725 closer to the target region. As shown in FIG. 11, the sample is moved to a position between the focal planes 720 and 722.

As another example, a second region $R_2$ of the same or different scan may be excited by light sources (e.g., lasers) configured to excite the first and second labels within the sample. After excitation, the imaging subsystem scans the region $R_2$ of the sample and obtains first and second images relating to the first and second labels, respectively. The imaging subsystem determines focus scores $FS_3$ and $FS_4$ for the first and second images, respectively. The imaging subsystem may analyze the focus scores $FS_3$ and $FS_4$ as described above and determine that the focus score $FS_4$ for the second label is greater than the focus score $FS_3$ for the first label. The imaging subsystem may also determine a difference in the focus scores $FS_3$ and $FS_4$. As such, the sample is located to the right of the target region (e.g., above the target region) as shown in FIG. 10. The sample and/or optical assembly may be moved relative to each other so that the sample is moved closer to the target region. The amount of movement may be based upon the difference between the focus scores $FS_3$ and $FS_4$. For example, the sample may be moved a shift Hz along the viewing axis 725 closer to the target region. As shown in FIG. 1, the sample is moved to a position between the focal planes 720 and 722.

As another example, the imaging subsystem may scan a region $R_3$ of the sample after excitation as described above. The region $R_3$ may be positioned within the target region of the imaging subsystem. The focus scores $FS_5$ and $FS_6$ of the images for the first and second labels, respectively, may both be within the $FS_{RANGE}$. The imaging subsystem may determine that the focus score $FS_5$ is greater than the focus score $FS_6$. The imaging subsystem may also determine a difference in the focus scores $FS_5$ and $FS_6$. As such, the sample and/or optical assembly may be moved relative to each other so that the sample is moved upward. For example, the sample may be moved a shift Iz along the viewing axis 725. However, the shift Iz may be smaller than the shift Gz and Hz because the difference between the focus scores $FS_5$ and $FS_6$ may be smaller than a predetermined amount.

FIG. 12 illustrates a method 800 in accordance with another embodiment. At 801, a method for controlling focus dynamically for an optical imager is initiated. At 802, first and second images of a scan region of a sample are obtained. The first image may include detected light emissions of a spectral band or channel from a first label, and the second image may include detected light emissions of a spectral band or channel from a second label. By way of example, the first label may be a FAM-type label and the second label may be a NIR-type label. The optical assembly may have different focal planes for the first and second labels.

In alternative embodiments, the first image may include detected light emissions from a spectral band or channel, but the second image may include detected light signals that were reflected or refracted by an optical substrate in the scan region.

At 803, the first and second images are analyzed to determine focus scores as described above. The focus scores of each image may be plotted along a focus score curve. Optionally, at 804, the focus score for at least one of the first and second labels is multiplied by a factor so that local maxima of the focus score curves are substantially equal. At 805, the first and second focus scores are compared. By comparing the first and second focus scores, the optical imager may determine whether the images acquired by the optical imager have an acceptable degree of focus. For example, if the focus score associated with the first label is greater than the focus score associated with the second label by a predetermined difference, then the optical imager may determine that the sample is located below a target region. If the focus score associated with the first label is less than the focus score associated with the second label by a predetermined difference, then the optical imager may determine that the sample is located above the target region. In some embodiments, the predetermined difference is any amount greater than zero.

At 806, the optical assembly and the sample are moved relative to each other based upon the comparison of the focus scores. The sample and the optical assembly may be moved relative to each other by a predetermined amount. In some embodiments, the predetermined amount is preset such that the optical assembly and the sample are moved relative to each other regardless of the difference between the focus scores. In other embodiments, a difference between the focus scores may facilitate determining an amount to move the sample and the optical assembly relative to each other. Additionally or alternatively, a difference between the focus score and the local maximum of the corresponding focus score curve may facilitate determining an amount to move the sample and the optical assembly relative to each other. At 807, the optical imager queries whether the scan is done. If the scan is not done, the optical imager may return to step 802 and repeat steps 802-806 for another scan region.

Before or during the method 800, the optical imager may be trained to determine the distance separating the local maxima of the focus curves. For example, the optical imager may determine the focus curves for a red spectral band and a green spectral band and also determine the optimal focal planes for both spectral bands. Before, after, or during the method 800, the optical imager may also be re-calibrated to facilitate maintaining the distance separating the local maxima of the focus curves.

Figure 13:
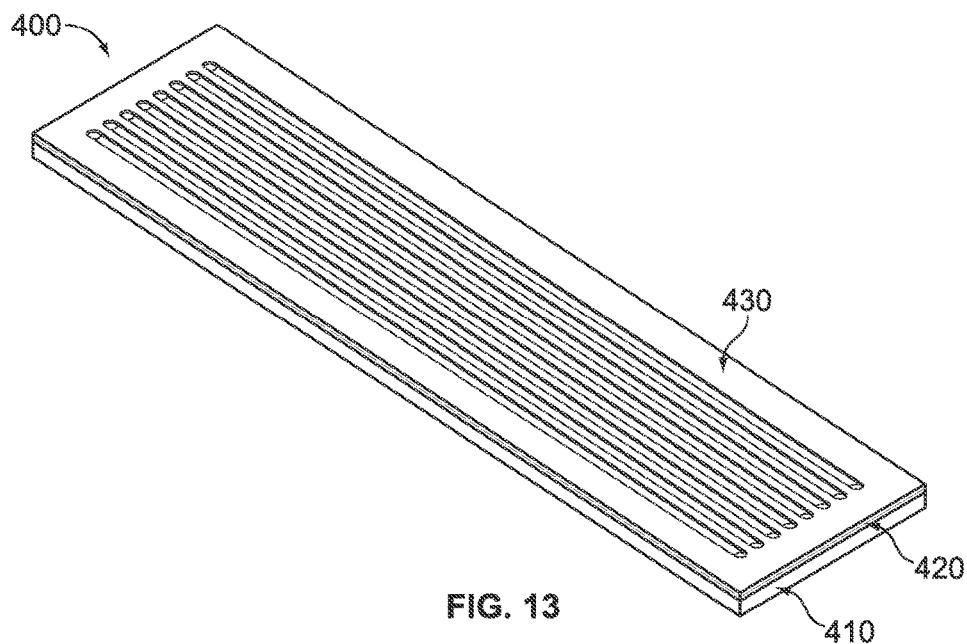
FIGS. 13 and 14 display an exemplary embodiment of a flowcell that may be utilized to carry samples in accordance with various embodiments.
Figure 14:
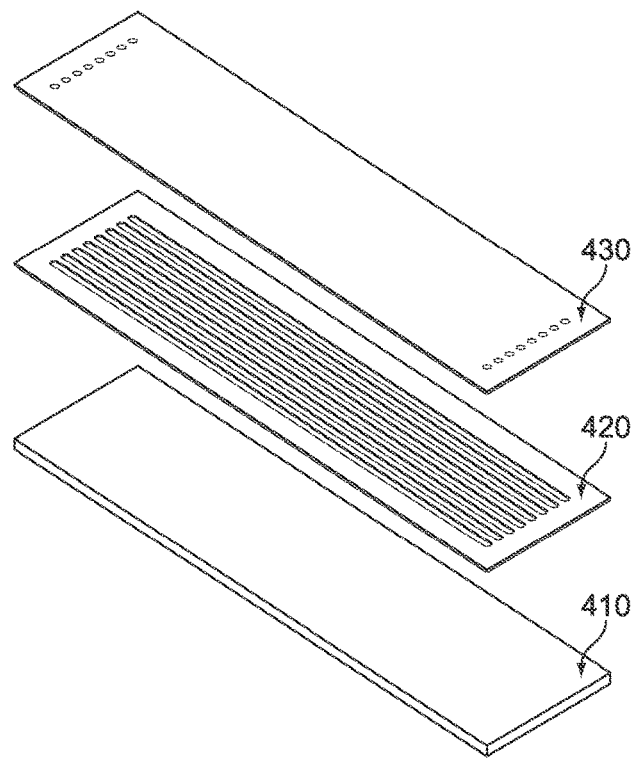

FIGS. 13 and 14 display one exemplary embodiment of a flowcell. The flowcell may be held at holder 118 to convey samples, such as sample 120. As can be seen, the particular flowcell embodiment, flowcell 400, comprises base layer 410 (e.g., of borosilicate glass 1000 μm in depth), channel layer 420 (e.g., of etched silicon 100 μm in depth) overlaid upon the base layer, and cover, or top, layer 430 (e.g., 300 μm in depth). When the layers are assembled together, enclosed channels are formed having inlets/outlets at either end through the cover. As will be apparent from the description of additional embodiments below, some flowcells can comprise openings for the channels on the bottom of the flowcell.

It will be appreciated that while particular flowcell configurations are presented herein, such configurations should not necessarily be taken as limiting. Thus, for example, various flowcells herein can comprise different numbers of channels (e.g., 1 channel, 2 or more channels, 4 or more channels, or 6, 8, 10, 16, or more channels, etc.). Additionally, various flowcells can comprise channels of different depths and/or widths (different both between channels in different flowcells and different between channels within the same flowcell). For example, while the channels formed in the cell in Figures 13-14 are 100 μm deep, other embodiments can optionally comprise channels of greater depth (e.g., 500 μm) or lesser depth (e.g., 50 μm).

The imaging system 10 may be configured to utilize diffraction grating based encoded optical identification elements (such as microbeads). The microbeads have embedded codes therein or thereon. The microbeads may be similar to or the same as those described in pending U.S. patent application Ser. No. 10/661,234, entitled Diffraction Grating Based Optical Identification Element, filed Sep. 12, 2003, which is incorporated herein by reference in its entirety, discussed more hereinafter. A bead cell may be similar to or the same as that described in pending U.S. patent application Ser. No. 10/661,836, entitled "Method and Apparatus for Aligning Microbeads in Order to Interrogate the Same", filed Sep. 12, 2003, and U.S. Pat. No. 7,164,533, entitled "Hybrid Random Bead/Chip Based Microarray", issued Jan. 16, 2007, as well as pending U.S. patent application Ser. No. 60/609,583, entitled "Improved Method and Apparatus for Aligning Microbeads in Order to Interrogate the Same", filed Sep. 13, 2004, Ser. No. 60/610,910, entitled "Method and Apparatus for Aligning Microbeads in Order to Interrogate the Same", filed Sep. 17, 2004, each of which is incorporated herein by reference in its entirety.

Figure 15:
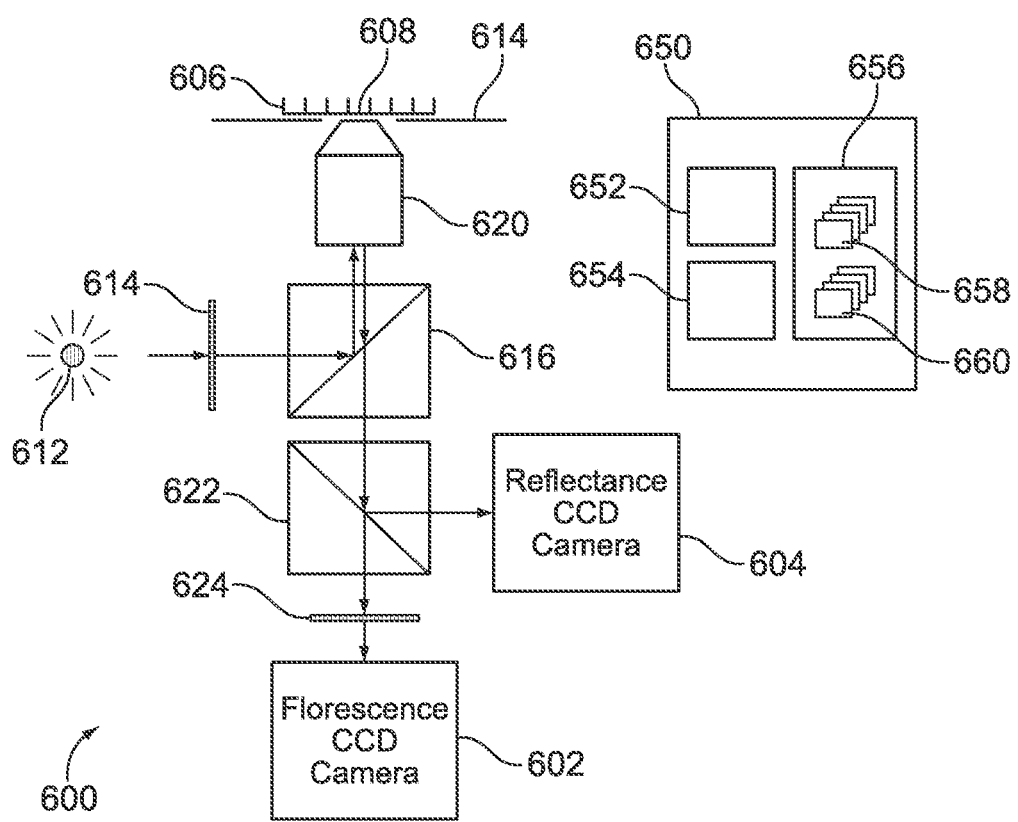
FIG. 15 illustrates an imaging system for detecting bioassays that is formed in accordance with an alternative embodiment.

FIG. 15 illustrates an imaging system 600 for detecting bioassays implemented in accordance with an alternative embodiment. The system 600 images encoded microparticles utilizing two CCD cameras 602 and 604 for the simultaneous acquisition of a reflectance and fluorescence image. The system 600 may be configured as an inverted epi-fluorescence microscope. A well plate 606 includes multiple wells 608 that are imaged. The well plate 606 is placed on a microscope stage 610. The stages 610 may correspond to holder 118 (FIG. 2) and the well plate may hold samples. The stage may move in x and y directions. Particles that have been dispensed into the well 608 in a fluid settle by gravity to the bottom surface. Each well 608 or groups of wells 608 may represent regions, for which images are acquired. Light coming from the light source 612 goes through the excitation filter 614 which selects the illuminating wavelength. The illuminating light reflects off the beam splitter 616 and travels up through the objective 620. The light returned to objective 620 may include emission and/or transmission light. The objective 620 may be moved in the z-direction to adjust the focal plane. The imaged area is referred to as the "field" or "field area". Reflected, transmitted, or emitted light (know together as the collection light) travels back down the objective and passes through the first beam splitter 616. The collection light then passes through the second beam splitter 622 which breaks it into the reflectance path and the fluorescence path. The emission filter 624 is located in the fluorescence path and selects the appropriate fluorescence emission wavelength. The light in the fluorescence path is recorded with the fluorescence CCD camera 602. The light in the reflectance path is recorded with the reflectance CCD camera 604.

The system 600 also includes a computer 650 having an image analysis module 652, a focus control module 654, and memory 656 that operate in the manner discussed above. The memory 656 stores the images 658 and 660 captured by the detectors 602 and 604. The analysis module 652 and the focus control module 654 perform the shifting, analyzing and adjusting operations discussed above in connection with the embodiment of FIGS. 2-6. For example, the focus control module 654 controls the z-distance between the objective 620 and the well plate 606. The focus control module 654 introduces shifts into the z-distance between the objective 620 and the well plate 606. The analysis module 652 analyzes the images 658 and/or 660 to identify the focus score associated with a well 608 and the focus control module 654 adjusts the z-distance before imaging the next well 608.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the specific components and processes described herein are intended to define the parameters of the various embodiments of the invention, they are by no means limiting and are exemplary embodiments. Many other embodiments will be apparent, to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

What is claimed is:

1. A method for scanning surface features of a microarray, comprising
   (a) providing a microarray to an optical scanner, wherein the microarray comprises a surface having features, wherein the features comprise different target molecules;
   (b) scanning the surface in the x or y direction to acquire optical signals from the features at sequential regions of the surface, wherein the focus setting in the z dimension between the optical scanner and the surface is dynamically controlled in real time by repeatedly
      (i) adding a predetermined focal offset in the z dimension,
      (ii) determining a focus score from the optical signals that are acquired at the predetermined focal offset, and
      (iii) adjusting the focus setting based on the focus score to reduce an error in the focus setting,
   thereby acquiring the optical signals from different regions at different degrees of focus such that a subset of the regions that are scanned have an introduced focus error; and
   (c) analyzing the optical signals that are obtained at the different degrees of focus to identify the different target molecules.

2. The method of claim 1, wherein step (b)(i) comprises periodically adding the predetermined focal offset.

3. The method of claim 1, wherein the optical signals that are used for the analyzing are the same optical signals that are used for the determining of the focus score.

4. The method of claim 1, wherein the determining of the focus score comprises determining an actual focal plane and a preferred focal plane for individual images of the microarray.

5. The method of claim 1, wherein the determining of the focus score comprises determining at least two focus scores and wherein the adjusting of the focus setting is based on the at least two focus scores.

6. The method of claim 1, wherein the adjusting of the focus setting comprises using an amplitude and phase of a transition in the focus score.

7. The method of claim 1, wherein the target molecules comprise nucleic acids.

8. The method of claim 7, wherein each of the features comprises an amplified population of a nucleic acid molecule template.

9. The method of claim 7, further comprising hybridizing the nucleic acids to probes at the features of the microarray prior to step (b).

10. The method of claim 7, wherein the features that comprise the nucleic acids are scanned during cycles of a nucleic acid sequencing reaction.

11. The method of claim 1, wherein the scanning comprises line scanning.

12. The method of claim 11, wherein the line scanning comprises time delay integration.

13. The method of claim 1, wherein the optical signals are acquired as an image of the microarray.

14. The method of claim 13, wherein the sequential regions of the microarray are non-overlapping and the acquiring of the optical signals at the sequential regions acquires a series of adjacent images that are separate and distinct from one another.

* * * * *